United States Patent
Li et al.

(10) Patent No.: US 10,398,893 B2
(45) Date of Patent: Sep. 3, 2019

(54) DISCONTINUOUS CONDUCTIVE FILLER POLYMER-MATRIX COMPOSITES FOR ELECTROMAGNETIC SHIELDING

(71) Applicant: MEDTRONIC, INC., Minneapolis, MN (US)

(72) Inventors: Bernard Li, Plymouth, MN (US);
Chad Cai, Woodbury, MN (US);
Xingfu Chen, Eden Prairie, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 394 days.

(21) Appl. No.: 14/717,881

(22) Filed: May 20, 2015

(65) Prior Publication Data

US 2015/0258335 A1 Sep. 17, 2015

Related U.S. Application Data

(62) Division of application No. 11/674,992, filed on Feb. 14, 2007, now Pat. No. 9,044,593.

(51) Int. Cl.
*A61N 1/05* (2006.01)
*A61N 1/08* (2006.01)

(52) U.S. Cl.
CPC .................. *A61N 1/08* (2013.01); *A61N 1/05* (2013.01); *A61N 1/0563* (2013.01); *A61N 1/086* (2017.08)

(58) Field of Classification Search
CPC .................. A61N 1/3718; A61N 2001/086
See application file for complete search history.

(56) References Cited

U.S. PATENT DOCUMENTS 2,433,480 A  12/1947  Rendich
2,487,038 A  11/1949  Jasper
(Continued)

FOREIGN PATENT DOCUMENTS

EP  0617978  10/1994
EP  0624383  11/1994
(Continued)

OTHER PUBLICATIONS

PCT/US2004/042081: Search Report and Written Opinion.
(Continued)

*Primary Examiner* — Michael J D Abreu
(74) *Attorney, Agent, or Firm* — Withers & Keys, LLC

(57) ABSTRACT

A medical electrical lead having a conductor assembly covered by an insulating layer, and a shield covering positioned adjacent or proximate to at least a portion of the insulating layer in order to shield the conductor assembly from one or more electromagnetic fields. The shield covering is formed of a polymer-matrix composite. The polymer-matrix composite includes a polymeric resin having discontinuous conductive fillers provided therein. The discontinuous conductive fillers include one or more of nano-sized metal structures and nano-sized non-metallic conductive structures. The nano-sized non-metallic conductive structures can have a coating formed of one or more metals. The nano-sized non-metallic conductive structures can be formed of carbon. In turn, the nano-sized non-metallic conductive structures can include one or more of carbon nanofibers, carbon filaments, carbon nanotubes, and carbon nanoflakes.

19 Claims, 10 Drawing Sheets

(56) References Cited

U.S. PATENT DOCUMENTS

| | | |
|---|---|---|
| 3,788,329 A | 1/1974 | Friedman |
| 3,842,485 A | 10/1974 | Bemert |
| 3,915,174 A | 10/1975 | Preston |
| 4,033,355 A | 7/1977 | Amundson |
| 4,038,990 A | 8/1977 | Thompson |
| 4,214,804 A | 7/1980 | Little |
| 4,220,813 A | 9/1980 | Kyle |
| 4,280,507 A | 7/1981 | Rosenberg |
| 4,320,763 A | 3/1982 | Money |
| 4,350,169 A | 9/1982 | Dutcher |
| 4,383,225 A | 5/1983 | Mayer |
| 4,403,824 A | 9/1983 | Scott |
| 4,441,498 A | 4/1984 | Nordling |
| 4,628,942 A | 12/1986 | Sweeney et al. |
| 4,683,895 A | 8/1987 | Pohndorf |
| 4,711,027 A | 12/1987 | Harris |
| 4,726,379 A | 2/1988 | Altman et al. |
| 4,852,585 A | 8/1989 | Heath |
| 4,906,241 A | 3/1990 | Noddin |
| 4,920,980 A | 5/1990 | Jackowski |
| 4,922,607 A | 5/1990 | Doan et al. |
| 4,934,380 A | 6/1990 | De Toledo |
| 4,947,866 A | 8/1990 | Lessar et al. |
| 4,951,672 A | 8/1990 | Buchwald et al. |
| 4,991,583 A | 2/1991 | Silvian |
| 5,003,992 A | 4/1991 | Holleman |
| 5,005,587 A | 4/1991 | Scott |
| 5,012,045 A | 4/1991 | Sato |
| 5,018,523 A | 5/1991 | Bach, Jr. et al. |
| 5,020,544 A | 6/1991 | Dahl et al. |
| 5,020,545 A | 6/1991 | Soukup |
| 5,036,862 A | 8/1991 | Pohndorf |
| 5,040,544 A | 8/1991 | Lessar et al. |
| 5,063,932 A | 11/1991 | Dahl et al. |
| 5,197,468 A | 3/1993 | Proctor et al. |
| 5,213,111 A | 5/1993 | Cook et al. |
| 5,217,010 A | 6/1993 | Tsitlik et al. |
| 5,231,078 A | 7/1993 | Riebman et al. |
| 5,243,996 A | 9/1993 | Hall |
| 5,246,438 A | 9/1993 | Langberg |
| 5,260,128 A | 11/1993 | Ishii et al. |
| 5,265,608 A | 11/1993 | Lee et al. |
| 5,265,623 A | 11/1993 | Kroll et al. |
| 5,271,417 A | 12/1993 | Swanson et al. |
| 5,308,664 A | 5/1994 | House et al. |
| 5,314,459 A | 5/1994 | Swanson et al. |
| 5,323,776 A | 6/1994 | Blakely et al. |
| 5,335,657 A | 8/1994 | Terry, Jr. et al. |
| 5,349,133 A | 9/1994 | Rogers |
| 5,360,441 A | 11/1994 | Otten |
| 5,366,496 A | 11/1994 | Dahl et al. |
| 5,370,644 A | 12/1994 | Langberg |
| 5,374,286 A | 12/1994 | Morris |
| 5,374,778 A | 12/1994 | Hashimoto et al. |
| 5,417,719 A | 5/1995 | Hull et al. |
| 5,456,705 A | 10/1995 | Morris |
| 5,458,629 A | 10/1995 | Baudino et al. |
| 5,458,631 A | 10/1995 | Xavier |
| 5,466,252 A | 11/1995 | Soukup et al. |
| 5,473,812 A | 12/1995 | Morris et al. |
| 5,476,496 A | 12/1995 | Strandberg et al. |
| 5,483,022 A | 1/1996 | Mar |
| 5,485,667 A | 1/1996 | Kleshinski |
| 5,500,013 A | 3/1996 | Buscemi et al. |
| 5,504,274 A | 4/1996 | McCabe et al. |
| 5,514,172 A | 5/1996 | Mueller |
| 5,515,848 A | 5/1996 | Corbett, III et al. |
| 5,523,534 A | 6/1996 | Meister et al. |
| 5,523,578 A | 6/1996 | Herskovic |
| 5,527,348 A | 6/1996 | Winkler |
| 5,534,018 A | 7/1996 | Wahlstrand |
| 5,552,565 A | 9/1996 | Cartier et al. |
| 5,571,157 A | 11/1996 | McConnell |
| 5,572,594 A | 11/1996 | DeVoe et al. |
| 5,591,218 A | 1/1997 | Jacobson |
| 5,594,304 A | 1/1997 | Graber |
| 5,606,981 A | 3/1997 | Tartacower et al. |
| 5,609,622 A | 3/1997 | Soukup et al. |
| 5,628,780 A | 5/1997 | Helland et al. |
| 5,629,622 A | 5/1997 | Scampini |
| 5,643,254 A | 7/1997 | Scheldrup et al. |
| 5,649,965 A | 7/1997 | Pons et al. |
| 5,662,697 A | 9/1997 | Li et al. |
| 5,676,659 A | 10/1997 | McGurk |
| 5,676,694 A | 10/1997 | Boser et al. |
| 5,683,435 A | 11/1997 | Truex et al. |
| 5,683,444 A | 11/1997 | Huntley et al. |
| 5,697,909 A | 12/1997 | Eggers et al. |
| 5,697,958 A | 12/1997 | Paul et al. |
| 5,702,437 A | 12/1997 | Baudino |
| 5,706,826 A | 1/1998 | Schwager |
| 5,722,998 A | 3/1998 | Prutchi et al. |
| 5,727,552 A | 3/1998 | Ryan |
| 5,751,539 A | 5/1998 | Stevenson et al. |
| 5,766,232 A | 6/1998 | Grevious et al. |
| 5,782,241 A | 7/1998 | Felblinger et al. |
| 5,795,341 A | 8/1998 | Samson |
| 5,807,258 A | 9/1998 | Cimochowski et al. |
| 5,814,076 A | 9/1998 | Brownlee |
| 5,827,997 A | 10/1998 | Chung et al. |
| 5,830,136 A | 11/1998 | Delonzor et al. |
| 5,842,966 A | 12/1998 | Markoll |
| 5,842,986 A | 12/1998 | Avrin et al. |
| 5,851,226 A | 12/1998 | Skubitz et al. |
| 5,897,584 A | 4/1999 | Herman |
| 5,905,627 A | 5/1999 | Brendel et al. |
| 5,927,345 A | 7/1999 | Samson |
| 5,931,861 A | 8/1999 | Werner et al. |
| 5,954,760 A | 9/1999 | Jarl |
| 5,964,705 A | 10/1999 | Truwit et al. |
| 5,968,087 A | 10/1999 | Hess |
| 5,970,429 A | 10/1999 | Martin |
| 5,942,966 A | 12/1999 | Markoll |
| 6,004,269 A | 12/1999 | Crowley et al. |
| 6,016,447 A | 1/2000 | Juran et al. |
| 6,024,703 A | 2/2000 | Zanelli et al. |
| 6,032,063 A | 2/2000 | Hoar et al. |
| 6,033,408 A | 3/2000 | Gage et al. |
| 6,055,457 A | 4/2000 | Bonner |
| 6,101,417 A | 8/2000 | Vogel et al. |
| 6,103,037 A | 8/2000 | Wilson |
| 6,108,582 A | 8/2000 | Fischer, Sr. |
| 6,132,390 A | 10/2000 | Cookston et al. |
| 6,141,593 A | 10/2000 | Patag |
| 6,143,013 A | 11/2000 | Samson et al. |
| 6,152,746 A | 11/2000 | Brown |
| 6,156,029 A | 12/2000 | Mueller |
| 6,195,267 B1 | 2/2001 | MacDonald et al. |
| 6,198,807 B1 | 3/2001 | DeSena |
| 6,198,972 B1 | 3/2001 | Hartlaub et al. |
| 6,209,764 B1 | 4/2001 | Hartlaub et al. |
| 6,240,322 B1 | 5/2001 | Peterfeso |
| 6,258,071 B1 | 7/2001 | Brookes |
| 6,265,466 B1 | 7/2001 | Glatkowski |
| 6,269,148 B1 | 7/2001 | Jessop et al. |
| 6,284,971 B1 | 9/2001 | Atalar et al. |
| 6,302,740 B1 | 10/2001 | Holmstrom |
| 6,348,070 B1 | 2/2002 | Teissl et al. |
| 6,424,234 B1 | 7/2002 | Stevenson |
| 6,471,699 B1 | 10/2002 | Fleischman et al. |
| 6,488,704 B1 | 12/2002 | Connelly et al. |
| 6,494,916 B1 | 12/2002 | Babalola et al. |
| 6,501,991 B1 | 12/2002 | Honeck et al. |
| 6,503,648 B1 | 1/2003 | Wang |
| 6,506,972 B1 | 1/2003 | Wang |
| 6,529,774 B1 | 3/2003 | Greene |
| 6,538,191 B1 | 3/2003 | MacDonald |
| 6,583,361 B2 | 6/2003 | Clouet |
| 6,606,521 B2 | 8/2003 | Paspa et al. |
| 6,640,137 B2 | 10/2003 | MacDonald |
| 6,648,690 B2 | 11/2003 | Saito et al. |
| 6,660,116 B2 | 12/2003 | Wolf et al. |
| 6,671,544 B2 | 12/2003 | Baudino |
| 6,671,554 B2 | 12/2003 | Gibson et al. |

(56) References Cited

U.S. PATENT DOCUMENTS

| | | |
|---|---|---|
| 6,673,999 B1 | 1/2004 | Wang et al. |
| 6,675,033 B1 | 1/2004 | Lardo et al. |
| 6,689,835 B2 | 2/2004 | Amarasekera et al. |
| 6,695,761 B2 | 2/2004 | Oschman et al. |
| 6,708,051 B1 | 3/2004 | Durousseau |
| 6,711,440 B2 | 3/2004 | Deal et al. |
| 6,712,844 B2 | 3/2004 | Pacetti et al. |
| 6,713,671 B1 | 3/2004 | Wang et al. |
| 6,718,203 B2 | 4/2004 | Weiner et al. |
| 6,718,207 B2 | 4/2004 | Connelly |
| 6,725,092 B2 | 4/2004 | MacDonald et al. |
| 6,735,471 B2 | 5/2004 | Hill et al. |
| 6,741,892 B1 | 5/2004 | Meadows et al. |
| 6,743,055 B1 | 6/2004 | Flynn |
| 6,750,055 B1 | 6/2004 | Connelly et al. |
| 6,757,566 B2 | 6/2004 | Weiner et al. |
| 6,760,628 B2 | 7/2004 | Weiner et al. |
| 6,763,268 B2 | 7/2004 | MacDonald et al. |
| 6,765,144 B1 | 7/2004 | Wang et al. |
| 6,768,053 B1 | 7/2004 | Wang et al. |
| 6,778,856 B2 | 8/2004 | Connelly et al. |
| 6,792,316 B2 | 9/2004 | Sass |
| 6,793,642 B2 | 9/2004 | Connelly et al. |
| 6,795,730 B2 | 9/2004 | Connelly et al. |
| 6,795,736 B2 | 9/2004 | Connelly et al. |
| 6,799,067 B2 | 9/2004 | Pacetti |
| 6,799,069 B2 | 9/2004 | Weiner et al. |
| 6,815,609 B1 | 11/2004 | Wang et al. |
| 6,819,954 B2 | 11/2004 | Connelly |
| 6,819,958 B2 | 11/2004 | Weiner et al. |
| 6,844,492 B1 | 1/2005 | Wang et al. |
| 6,845,259 B2 | 1/2005 | Pacetti et al. |
| 6,845,267 B2 | 1/2005 | Harrison et al. |
| 6,846,985 B2 | 1/2005 | Wang et al. |
| 6,850,805 B2 | 2/2005 | Connelly et al. |
| 6,852,091 B2 | 2/2005 | Edwards et al. |
| 6,863,653 B1 | 3/2005 | Zanelli et al. |
| 6,864,418 B2 | 3/2005 | Wang et al. |
| 6,869,683 B2 | 3/2005 | Sakurai et al. |
| 6,871,091 B2 | 3/2005 | Wilkinson et al. |
| 6,872,882 B2 | 3/2005 | Fritz |
| 6,875,180 B2 | 4/2005 | Weiner et al. |
| 6,879,861 B2 | 4/2005 | Benz et al. |
| 6,882,519 B2 | 4/2005 | Uzawa et al. |
| 6,895,280 B2 | 5/2005 | Meadows et al. |
| 6,901,287 B2 | 5/2005 | Davis et al. |
| 6,901,290 B2 | 5/2005 | Foster et al. |
| 6,906,256 B1 | 6/2005 | Wang |
| 6,920,361 B2 | 7/2005 | Williams |
| 6,922,590 B1 | 7/2005 | Whitehurst |
| 6,925,328 B2 | 8/2005 | Foster et al. |
| 6,930,242 B1 | 8/2005 | Helfer |
| 6,937,906 B2 | 8/2005 | Terry et al. |
| 6,944,489 B2 | 9/2005 | Zeiljemaker et al. |
| 6,949,929 B2 | 9/2005 | Gray et al. |
| 6,954,674 B2 | 10/2005 | Connelly |
| 6,968,235 B2 | 11/2005 | Belden et al. |
| 6,968,236 B2 | 11/2005 | Hagele |
| 6,971,391 B1 | 12/2005 | Wang et al. |
| 6,980,865 B1 | 12/2005 | Wang et al. |
| 6,982,378 B2 | 1/2006 | Dickson |
| 6,985,775 B2 | 1/2006 | Reinke et al. |
| 6,993,387 B2 | 1/2006 | Connelly et al. |
| 6,999,818 B2 | 2/2006 | Stevenson et al. |
| 6,999,821 B2 | 2/2006 | Jenney et al. |
| 7,001,369 B2 | 2/2006 | Griffin et al. |
| 7,013,174 B2 | 3/2006 | Connelly et al. |
| 7,013,180 B2 | 3/2006 | Villaseca et al. |
| 7,015,392 B1 | 3/2006 | Dickenson |
| 7,015,393 B2 | 3/2006 | Weiner |
| 7,047,084 B2 | 5/2006 | Erickson |
| 7,050,855 B2 | 5/2006 | Zeijlemaker et al. |
| 7,058,192 B2 | 6/2006 | Muller et al. |
| 7,076,283 B2 | 7/2006 | Cho et al. |
| 7,076,302 B2 | 7/2006 | Scheiner |
| 7,082,328 B2 | 7/2006 | Funke |
| 7,082,337 B2 | 7/2006 | Sommer et al. |
| 7,103,413 B2 | 9/2006 | Swanson |
| 7,113,827 B2 | 9/2006 | Silvestri |
| 7,115,134 B2 | 10/2006 | Chambers |
| 7,118,693 B2 | 10/2006 | Glatkowski et al. |
| 7,123,013 B2 | 10/2006 | Gray |
| 7,125,409 B2 | 10/2006 | Truckai et al. |
| 7,162,302 B2 | 1/2007 | Wang et al. |
| 7,174,219 B2 | 2/2007 | Wahlstrand et al. |
| 7,187,980 B2 | 3/2007 | Osypka et al. |
| 7,233,825 B2 | 6/2007 | Jorgenson et al. |
| 7,257,449 B2 | 8/2007 | Bodner |
| 7,282,260 B2 | 10/2007 | LeGrande et al. |
| 7,286,871 B2 | 10/2007 | Cohen |
| 7,286,882 B2 | 10/2007 | Cole |
| 7,292,894 B2 | 11/2007 | Belden |
| 7,294,785 B2 | 11/2007 | Uutela et al. |
| 7,319,901 B2 | 1/2008 | Dublin |
| 7,363,090 B2 | 4/2008 | Halperin |
| 7,389,148 B1 | 6/2008 | Morgan |
| 7,540,865 B2 | 6/2009 | Griffin et al. |
| 7,548,788 B2 | 6/2009 | Chinn et al. |
| 7,591,831 B2 | 9/2009 | Parsonage et al. |
| 7,674,972 B2 | 3/2010 | Gladd et al. |
| 7,711,436 B2 | 5/2010 | Stone |
| 7,729,777 B2 | 6/2010 | Gray et al. |
| 7,738,942 B2 | 6/2010 | Weiner |
| 7,813,811 B2 | 10/2010 | Wingeier et al. |
| 7,819,826 B2 | 10/2010 | Diederich et al. |
| 7,822,484 B1 | 10/2010 | Zhao et al. |
| 7,828,833 B2 | 11/2010 | Haverkost |
| 7,844,343 B2 | 11/2010 | Wahlstrand |
| 7,844,344 B2 | 11/2010 | Wahlstrand |
| 7,853,332 B2 | 12/2010 | Olsen |
| 7,877,150 B2 | 1/2011 | Hoegh et al. |
| 7,904,178 B2 | 3/2011 | Williams |
| 7,917,213 B2 | 3/2011 | Bulkes |
| 7,933,652 B2 | 4/2011 | Phillips |
| 8,007,440 B2 | 8/2011 | Magnin et al. |
| 8,027,736 B2 | 9/2011 | Wahlstrand |
| 8,036,756 B2 | 10/2011 | Swoyer et al. |
| 8,048,060 B2 | 11/2011 | Griffin et al. |
| 8,055,351 B2 | 11/2011 | Atalar et al. |
| 8,106,657 B2 | 1/2012 | Sakellariou et al. |
| 8,170,691 B2 | 5/2012 | Eckerdal |
| 8,202,259 B2 | 6/2012 | Evans et al. |
| 8,246,643 B2 | 8/2012 | Nita |
| 8,275,464 B2 | 9/2012 | Li et al. |
| 8,280,526 B2 | 10/2012 | Wahlstrand |
| 8,483,842 B2 | 7/2013 | Alexander et al. |
| 8,620,455 B2 | 12/2013 | Alexander et al. |
| 8,676,340 B2 | 3/2014 | Wahlstrand |
| 8,744,598 B2 | 6/2014 | Alexander et al. |
| 8,788,061 B2 | 7/2014 | Mehdizadeth |
| 8,805,534 B2 | 8/2014 | Olsen |
| 8,903,504 B2 | 12/2014 | Hegland |
| 9,002,474 B2 | 4/2015 | Olsen |
| 9,037,263 B2 | 5/2015 | Marshall |
| 9,044,593 B2 | 6/2015 | Li |
| 2001/0044646 A1 | 11/2001 | Marshall et al. |
| 2002/0032468 A1 | 3/2002 | Hill |
| 2002/0038135 A1 | 3/2002 | Connelly et al. |
| 2002/0058978 A1 | 5/2002 | Sass |
| 2002/0183438 A1 | 5/2002 | Amarasekera et al. |
| 2002/0082673 A1 | 6/2002 | Benz et al. |
| 2002/0106918 A1 | 8/2002 | Saito et al. |
| 2002/0111659 A1 | 8/2002 | Davis et al. |
| 2002/0111663 A1 | 8/2002 | Dahl et al. |
| 2002/0116028 A1 | 8/2002 | Greatbatch et al. |
| 2002/0116029 A1 | 8/2002 | Miller et al. |
| 2002/0116033 A1 | 8/2002 | Greatbatch et al. |
| 2002/0116034 A1 | 8/2002 | Miller et al. |
| 2002/0128689 A1 | 9/2002 | Connelly et al. |
| 2002/0128691 A1 | 9/2002 | Connelly |
| 2002/0133086 A1 | 9/2002 | Connelly et al. |
| 2002/0133199 A1 | 9/2002 | MacDonald et al. |
| 2002/0133200 A1 | 9/2002 | Weiner et al. |
| 2002/0133201 A1 | 9/2002 | Connelly et al. |

(56) References Cited

U.S. PATENT DOCUMENTS

| | | |
|---|---|---|
| 2002/0133202 A1 | 9/2002 | Connelly et al. |
| 2002/0133208 A1 | 9/2002 | Connelly |
| 2002/0133211 A1 | 9/2002 | Weiner et al. |
| 2002/0133216 A1 | 9/2002 | Connelly et al. |
| 2002/0138102 A1 | 9/2002 | Weiner et al. |
| 2002/0138107 A1 | 9/2002 | Weiner et al. |
| 2002/0138108 A1 | 9/2002 | Weiner et al. |
| 2002/0138110 A1 | 9/2002 | Connelly et al. |
| 2002/0138112 A1 | 9/2002 | Connelly et al. |
| 2002/0143377 A1 | 10/2002 | Wessman et al. |
| 2002/0183740 A1 | 12/2002 | Edwards et al. |
| 2002/0183822 A1 | 12/2002 | Bodner |
| 2002/0188345 A1 | 12/2002 | Pacetti |
| 2003/0009207 A1 | 1/2003 | Paspa et al. |
| 2003/0014080 A1 | 1/2003 | Baudino |
| 2003/0036776 A1 | 2/2003 | Foster et al. |
| 2003/0044623 A1 | 3/2003 | Sakurai et al. |
| 2003/0045920 A1 | 3/2003 | Belden et al. |
| 2003/0060732 A1 | 3/2003 | Jacobsen et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0093107 A1 | 5/2003 | Parsonage et al. |
| 2003/0109901 A1 | 6/2003 | Greatbatch |
| 2003/0117787 A1 | 6/2003 | Nakauchi |
| 2003/0120148 A1 | 6/2003 | Pacetti |
| 2003/0120197 A1 | 6/2003 | Kaneko et al. |
| 2003/0135114 A1 | 7/2003 | Pacetti et al. |
| 2003/0139794 A1 | 7/2003 | Jenney et al. |
| 2003/0139806 A1 | 7/2003 | Haverkost et al. |
| 2003/0140931 A1 | 7/2003 | Zeijlemaker |
| 2003/0144704 A1 | 7/2003 | Terry |
| 2003/0144705 A1 | 7/2003 | Funke |
| 2003/0144716 A1 | 7/2003 | Reinke et al. |
| 2003/0144717 A1 | 7/2003 | Hegele |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0167052 A1 | 9/2003 | Lee et al. |
| 2003/0204217 A1 | 10/2003 | Greatbatch |
| 2003/0225331 A1 | 12/2003 | Diederich et al. |
| 2004/0020674 A1 | 2/2004 | McFadden et al. |
| 2004/0024442 A1 | 2/2004 | Sowinski et al. |
| 2004/0028859 A1 | 2/2004 | LeGrande et al. |
| 2004/0068307 A1 | 4/2004 | Goble |
| 2004/0071949 A1 | 4/2004 | Glatkowski et al. |
| 2004/0088012 A1 | 5/2004 | Kroll et al. |
| 2004/0106958 A1 | 6/2004 | Mathis et al. |
| 2004/0162600 A1 | 8/2004 | Williams |
| 2004/0167443 A1 | 8/2004 | Shireman et al. |
| 2004/0173368 A1 | 9/2004 | Dickson |
| 2004/0199069 A1* | 10/2004 | Connelly ............ G01R 33/285 600/412 |
| 2004/0220549 A1 | 11/2004 | Dittman et al. |
| 2004/0249428 A1 | 12/2004 | Wang et al. |
| 2004/0251042 A1 | 12/2004 | Weiner et al. |
| 2004/0263172 A1 | 12/2004 | Gray et al. |
| 2004/0263173 A1 | 12/2004 | Gray |
| 2004/0263174 A1 | 12/2004 | Gray et al. |
| 2004/0267328 A1 | 12/2004 | Duffin |
| 2005/0065587 A1 | 3/2005 | Gryzwa |
| 2005/0070972 A1 | 3/2005 | Wahlstrand |
| 2005/0080471 A1 | 4/2005 | Chitre et al. |
| 2005/0113876 A1 | 5/2005 | Weiner |
| 2005/0115624 A1 | 6/2005 | Walak |
| 2005/0137664 A1 | 6/2005 | Sommer et al. |
| 2005/0145307 A1 | 7/2005 | Shireman et al. |
| 2005/0159661 A1 | 7/2005 | Connelly et al. |
| 2005/0182471 A1 | 8/2005 | Wang |
| 2005/0222642 A1 | 10/2005 | Przybyszewski |
| 2005/0222647 A1 | 10/2005 | Wahlstrand |
| 2005/0222656 A1 | 10/2005 | Wahlstrand |
| 2005/0222657 A1 | 10/2005 | Wahlstrand |
| 2005/0222658 A1 | 10/2005 | Hoegh et al. |
| 2005/0222659 A1 | 10/2005 | Olsen |
| 2006/0030918 A1 | 2/2006 | Chinn et al. |
| 2006/0036306 A1 | 2/2006 | Heist et al. |
| 2006/0079926 A1 | 4/2006 | Desai et al. |
| 2006/0089680 A1 | 4/2006 | Bruchmann et al. |
| 2006/0095078 A1 | 5/2006 | Tronnes |
| 2006/0135962 A1 | 6/2006 | Kick et al. |
| 2006/0155270 A1 | 7/2006 | Hancock |
| 2006/0167522 A1 | 7/2006 | Malinowski |
| 2006/0167527 A1 | 7/2006 | Malinowski |
| 2006/0200218 A1 | 9/2006 | Wahlstrand |
| 2006/0224207 A1 | 10/2006 | Dublin |
| 2006/0247747 A1 | 11/2006 | Olsen |
| 2006/0247748 A1 | 11/2006 | Wahlstrand |
| 2007/0021811 A1 | 1/2007 | D'Aquanni et al. |
| 2007/0106332 A1 | 5/2007 | Denker |
| 2007/0123805 A1 | 5/2007 | Shireman et al. |
| 2007/0129779 A1 | 6/2007 | Ayre |
| 2007/0168008 A1 | 7/2007 | Olsen |
| 2007/0185556 A1 | 8/2007 | Williams |
| 2007/0208383 A1 | 9/2007 | Williams |
| 2007/0293924 A1 | 12/2007 | Belden et al. |
| 2008/0033497 A1 | 2/2008 | Bulkes |
| 2008/0039709 A1 | 2/2008 | Karmarkar |
| 2008/0058715 A1 | 3/2008 | Houser et al. |
| 2008/0154326 A1 | 6/2008 | Clyne |
| 2008/0183263 A1 | 7/2008 | Alexander |
| 2008/0195186 A1 | 8/2008 | Li |
| 2008/0195187 A1 | 8/2008 | Li |
| 2008/0215008 A1 | 9/2008 | Nance et al. |
| 2008/0242944 A1 | 10/2008 | Sharma |
| 2008/0243081 A1 | 10/2008 | Nance et al. |
| 2008/0243218 A1 | 10/2008 | Bottomley |
| 2008/0262582 A1 | 10/2008 | Alexander |
| 2008/0262584 A1 | 10/2008 | Bottomley |
| 2008/0269863 A1 | 10/2008 | Alexander |
| 2008/0287804 A1 | 11/2008 | Nita |
| 2009/0204192 A1 | 8/2009 | Carlton |
| 2009/0221970 A1 | 9/2009 | Spinoza |
| 2009/0228074 A1 | 9/2009 | Edgell et al. |
| 2009/0234402 A1 | 9/2009 | Marshall |
| 2009/0240235 A1 | 9/2009 | Murata |
| 2009/0259272 A1 | 10/2009 | Reddy |
| 2009/0270956 A1 | 10/2009 | Vase |
| 2009/0287189 A1 | 11/2009 | Suwito |
| 2010/0069743 A1 | 3/2010 | Sheetz et al. |
| 2010/0100164 A1 | 4/2010 | Johnson et al. |
| 2010/0137957 A1 | 6/2010 | Eckerdal |
| 2010/0145426 A1 | 6/2010 | Stone |
| 2010/0198327 A1 | 8/2010 | Helland |
| 2010/0256528 A1 | 10/2010 | Lippert et al. |
| 2010/0256604 A1 | 10/2010 | Lippert et al. |
| 2010/0268310 A1 | 10/2010 | Bonde et al. |
| 2010/0331938 A1 | 12/2010 | Sommer |
| 2011/0015713 A1 | 1/2011 | Min |
| 2011/0034983 A1 | 2/2011 | Min |
| 2011/0071599 A1 | 3/2011 | Olsen |
| 2011/0071604 A1 | 3/2011 | Wahlstrand |
| 2011/0071605 A1 | 3/2011 | Wahlstrand |
| 2011/0112615 A1 | 5/2011 | Hoegh et al. |
| 2011/0160818 A1* | 6/2011 | Struve ................ A61N 1/3718 607/116 |
| 2011/0230943 A1 | 9/2011 | Johnson et al. |
| 2011/0251487 A1 | 10/2011 | Magnin et al. |
| 2011/0319905 A1 | 12/2011 | Palme et al. |
| 2012/0010689 A1 | 1/2012 | Wahlstrand |
| 2012/0035616 A1* | 2/2012 | Olsen ................ A61N 1/3718 606/129 |
| 2012/0035694 A1 | 2/2012 | Olsen |
| 2012/0035695 A1 | 2/2012 | Olsen et al. |
| 2012/0035696 A1 | 2/2012 | Kern |
| 2012/0035697 A1 | 2/2012 | Stone |
| 2012/0035951 A1 | 2/2012 | Goetz |
| 2012/0041528 A1 | 2/2012 | Mehdizadeh et al. |
| 2012/0041529 A1 | 2/2012 | Olsen |
| 2012/0046722 A1 | 2/2012 | Olsen |
| 2012/0635696 | 2/2012 | Kern |
| 2012/0053664 A1 | 3/2012 | Hegland |
| 2012/0059467 A1 | 3/2012 | Drew |

(56) References Cited

U.S. PATENT DOCUMENTS

| | | |
|---|---|---|
| 2012/0130461 A1 | 5/2012 | Olsen |
| 2012/0330383 A1 | 12/2012 | Wahlstrand |
| 2013/0296991 A1 | 11/2013 | Alexander et al. |
| 2014/0107746 A1 | 4/2014 | Alexander et al. |
| 2014/0200643 A1 | 7/2014 | Wahlstrand |
| 2014/0288626 A1 | 9/2014 | Alexander et al. |
| 2014/0345132 A1 | 11/2014 | Mehdizadeh et al. |
| 2014/0350654 A1 | 11/2014 | Olsen et al. |
| 2015/0082618 A1 | 3/2015 | Hegland |
| 2015/0270792 A1 | 6/2015 | Alford |

FOREIGN PATENT DOCUMENTS

| | | |
|---|---|---|
| EP | 0713714 | 5/1996 |
| EP | 0760196 | 3/1997 |
| EP | 0920239 | 6/1999 |
| EP | 1273922 | 1/2003 |
| EP | 1424095 | 6/2004 |
| EP | 1466576 | 10/2004 |
| EP | 1625875 | 2/2006 |
| EP | 1632265 | 3/2006 |
| EP | 1935449 | 6/2008 |
| GB | 2429154 | 2/2007 |
| JP | 07/255863 | 10/1995 |
| JP | 11-086641 | 3/1999 |
| JP | 11/086641 | 3/1999 |
| WO | WO95/032673 | 12/1995 |
| WO | WO96/016694 | 6/1996 |
| WO | WO96/028951 | 9/1996 |
| WO | WO97/041923 | 11/1997 |
| WO | WO98/048896 | 11/1998 |
| WO | WO99/010035 | 3/1999 |
| WO | WO99/019020 | 4/1999 |
| WO | WO99/060370 | 11/1999 |
| WO | WO00/027279 | 5/2000 |
| WO | WO01/080940 | 11/2001 |
| WO | WO02/000292 | 1/2002 |
| WO | WO02/083236 | 10/2002 |
| WO | WO03/037429 | 5/2003 |
| WO | WO03/061755 | 7/2003 |
| WO | WO03/063946 | 8/2003 |
| WO | WO03/063948 | 8/2003 |
| WO | WO03/063952 | 8/2003 |
| WO | WO03/063953 | 8/2003 |
| WO | WO03/063954 | 8/2003 |
| WO | WO03/063955 | 8/2003 |
| WO | WO03/063956 | 8/2003 |
| WO | WO03/063957 | 8/2003 |
| WO | WO03/075797 | 9/2003 |
| WO | WO03/092326 | 11/2003 |
| WO | WO03/095022 | 11/2003 |
| WO | WO04/012809 | 2/2004 |
| WO | WO04/052448 | 6/2004 |
| WO | WO04/073040 | 8/2004 |
| WO | WO05/030322 | 4/2005 |
| WO | WO05/032654 | 4/2005 |
| WO | WO05/102444 | 11/2005 |
| WO | WO05/102445 | 11/2005 |
| WO | WO05/102446 | 11/2005 |
| WO | WO05/102447 | 11/2005 |
| WO | WO06/031317 | 3/2006 |
| WO | WO06/093685 | 9/2006 |
| WO | WO06/093686 | 9/2006 |
| WO | WO06/118640 | 11/2006 |
| WO | WO06/118641 | 11/2006 |
| WO | WO07/047966 | 4/2007 |
| WO | WO07/124273 | 11/2007 |
| WO | WO07/126657 | 11/2007 |
| WO | WO07/149757 | 12/2007 |
| WO | WO08/088568 | 7/2008 |
| WO | WO08/100839 | 8/2008 |
| WO | WO08/100840 | 8/2008 |
| WO | WO08/111986 | 9/2008 |
| WO | WO08/130409 | 10/2008 |
| WO | WO08/134196 | 11/2008 |
| WO | WO08/140376 | 11/2008 |
| WO | WO09/011440 | 9/2009 |
| WO | WO09/134901 | 11/2009 |
| WO | WO10/062988 | 6/2010 |
| WO | WO10/126871 | 11/2010 |
| WO | WO10/126877 | 11/2010 |
| WO | WO10/126884 | 11/2010 |
| WO | WO10/126887 | 11/2010 |
| WO | WO10/126935 | 11/2010 |
| WO | WO10/126939 | 11/2010 |
| WO | WO10/126943 | 11/2010 |
| WO | WO10/126946 | 11/2010 |
| WO | WO10/126949 | 11/2010 |
| WO | WO10/126975 | 11/2010 |
| WO | WO10/135440 | 11/2010 |
| WO | WO11/019416 | 2/2011 |
| WO | WO12/103419 | 8/2012 |
| WO | WO13/158189 | 10/2013 |

OTHER PUBLICATIONS

PCT/US2005/000322: Search Report and Written Opinion.
PCT/US2008/053540: Search Report and Written Opinion.
PCT/US2008/053541: Search Report and Written Opinion.
PCT/US2008/059358: Search Report and Written Opinion.
PCT/US2009/036461: Search Report and Written Opinion.
PCT/US2010/032516: Search Report and Written Opinion.
PCT/US2010/032526: Search Report and Written Opinion.
PCT/US2010/032543: Search Report and Written Opinion.
PCT/US2010/032560: Search Report and Written Opinion.
PCT/US2010/032567: Search Report and Written Opinion.
PCT/US2010/032666: Search Report and Written Opinion.
PCT/US2010/032671: Search Report and Written Opinion.
PCT/US2010/032675: Search Report and Written Opinion.
PCT/US2010/032682: Search Report and Written Opinion.
PCT/US2010/032719: Search Report and Written Opinion.
PCT/US2013/023637: Search Report and Written Opinion.
Baker et al., "Evaluation of Specific Absorption Rates as a Dosimeter of MRI-Related Implant Heating", Journal of Magnetic Resonance Imaging 20:315-320 (2004).
Baker, K., et al., "Neurostimulation Systems: Assessment of Magnetic Field Interactions Associated with 1.5 and 3-Tesla MR Systems", J. Magn. Reson. Imaging, Jan. 2005, 21(1);72-7.
Chung, D.D.L., "Carbon Fiber Composites", 1994, chapter 1, p. 8, table 1.2, Elsevier, ISBN: 978-0-7506-9169-7.
Chung, D.D.L., Comparison of Submicron-Diameter Carbon Filaments and Conventional Carbon Fibers as Fillers in Composite Materials, Carbon 39 (2001) pp. 1119-1125, Elsevier Science Ltd.
Chung, D.D.L., Electromagnetic Interference Shielding Effectiveness of Carbon Materials, Carbon 29 (2001) pp. 279-285, Elsevier Science Ltd.
Engdahl, Tomi, "Ground Loop Basics." Web Jan. 4, 2009, ePanorama.net www.epanorama.net/documents/groundloop/basics.html U.S. Appl. No. 11/739,787.
Finelli, D., et al., "MRI Imaging-Related Heating of Deep Brain Stimulation Electrodes: In Vitro Study", AJNR Am. J. Neuroadiol 23:1, Nov./Dec. 2002.
Jou, W.S. "A Novel Structure of Woven Continuous-Carbon Fiber Composites with High Electromagnetic Shielding", Journal of Electronic Materials, vol. 33, No. 3, Mar. 1, 2004, pp. 162-170(9), Minerals, Metals and Materials Society, http://findarticles.com/p/articles/mi_qu3776/is_200403/ai_n9405_582/print.
Kolin, et al., "An Electromagnetic Catheter Flow Meter for Determination of Blood Flow in Major Arteries," Department of Biophysics, Physiology, and Radiology, University of California School of Medicine (Los Angeles) Jan. 19, 1988, Proc. N.A.S. vol. 59, pp. 808-815.
Kolin, et al., "An Electromagnetic Intravascular Blood-Flow Sensor", Department of Biophysics, University of California School of Medicine (Los Angeles), Mar. 20, 1967, Proc. N.A.S., vol. 57, pp. 1331-1337.
Kolin, et al., "Miniaturization of the Electromagnetic Blood Flow Meter and its Use for the Recording of Circulatory Responses of

(56) References Cited

OTHER PUBLICATIONS

Conscious Animals to Sensory Stimuli", Department of Biophysics, University of California at Los Angeles, Aug. 1959, Proc. N.A.S. vol. 45(8), pp. 1312-1321.

Medtronic Activa Product Family and Procedure Solution Brochure, Medtronic, Inc, 2001.

Medtronic Neurostimulation Systems Brochure, Medtronic, Inc., 2002.

Quick et al., "Endourethral MRI", Magnetic Resonance in Medicine, 45:138-146, 2001.

Rezai, A., et al., "Neurostimulation System Used for Deep Brain Stimulation (DBS): MR Safety Issues and Implications of Failing to Follow Safety Recommendations" Investigative Radiology, May 2004, vol. 39, Issue 5, pp. 300-303.

Rezai, A., et al., "Neurostimulation Systems for Deep Brain Stimulation In Vitro Evaluation of Magnetic Resonance Imaging-Related Healing at 1.5 Tesla", Journal of Magnetic Reson. Imaging 2002; 15:241-50.

\* cited by examiner

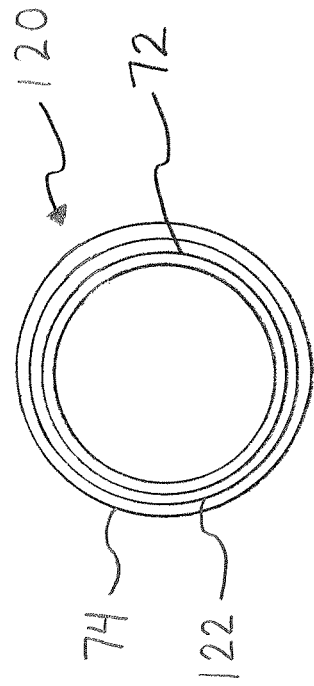
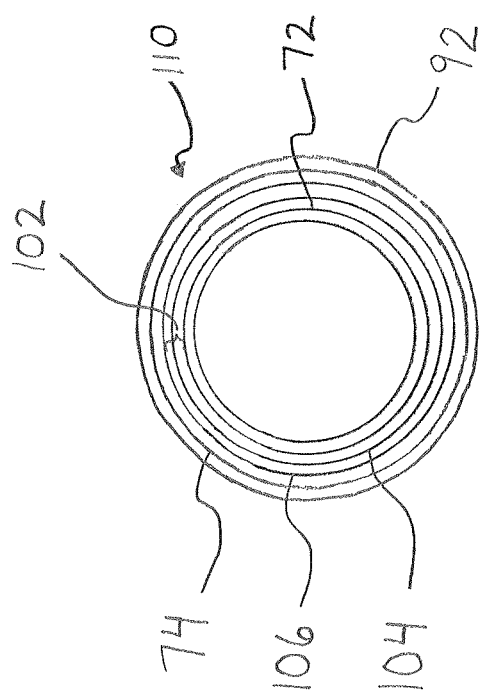

DISCONTINUOUS CONDUCTIVE FILLER POLYMER-MATRIX COMPOSITES FOR ELECTROMAGNETIC SHIELDING

FIELD

The present invention relates generally to medical devices, and, more particularly, to reducing the effects of electromagnetic radiation on such medical devices.

BACKGROUND

Since their earliest inception, implantable medical devices (IMDs) have continually been advanced in significant ways. Today, IMDs include therapeutic and diagnostic devices, such as pacemakers, cardioverter/defibrillators, hemodynamic monitors, neurostimulators, and drug administering devices, as well as other devices for alleviating the adverse effects of various health ailments.

As is known, modern electrical therapeutic and diagnostic devices for the heart and other areas of the body generally include an electrical connection between the device and the body. This connection is usually provided by at least one medical electrical lead. For example, a neurostimulator delivers mild electrical impulses to neural tissue using one or more electrical leads. In turn, such neurostimulation often results in effective pain relief and a reduction in the use of pain medications and/or repeat surgeries. Each electrical lead used with such devices typically takes the form of a long, generally straight, flexible, insulated conductor. At its proximal end, the lead is typically connected to a connector of the device, which also may be implanted within the patient's body. Generally, one or more electrodes are located at or near the distal end of the lead and are attached to, or otherwise come in contact with, the body. Such devices may be controlled by a physician or a patient through the use of an external programmer.

It is well known that, if not shielded sufficiently, the implanted leads of medical devices can be adversely affected when a patient is exposed to alternating electromagnetic fields. Alternating electromagnetic fields can generally stem from any of a number of radio-frequency radiation sources, e.g., magnetic resonance imaging (MRI) systems as described below. As such, if an implanted medical lead is not sufficiently shielded, electromagnetic fields can induce an electric current within a conductor of the lead. In turn, such an implanted electrical lead would act as an antenna, resulting in an electrical current that flows from the electrode of the lead and through body tissue. Because the tissue area associated with electrode contact may be very small, the current densities may be high, which can result in tissue heating that may cause damage.

There can be other limitations associated with exposing implanted leads of medical devices to electromagnetic fields and/or radio-frequency energy if the leads are not sufficiently shielded therefrom. As is known, a sudden burst of radio-frequency energy can cause an electric pulse within the lead. The medical device, as should be appreciated, can sense the imposed voltage on the lead, and in turn, may cause the device to respond inappropriately, resulting in the wrong therapy being administered to the patient at that time or in the future. For example, with respect to cardiac IMDs, inappropriate therapy modification may be one response of the IMD, which can involve changing the rate or thresholds associated with pacing pulses.

As is known, magnetic resonance imaging (MRI) is an anatomical imaging tool which utilizes non-ionizing radiation (i.e., no x-rays or gamma rays) and provides a non-invasive method for the examination of internal structure and function. For example, MRI permits the study of the overall function of the heart in three dimensions significantly better than any other imaging method. Furthermore, MRI scanning is widely used in the diagnosis of diseases and injuries to the head. Magnetic resonance spectroscopic imaging (MRSI) systems are also known and are herein intended to be included within the terminology "MRI" systems or scanners. These MRI systems can be used to give valuable diagnostic information, but also subject the patient to significant alternating electromagnetic fields and/or radio-frequency energy, which may result in one or more of the undesirable effects described above with respect to IMDs or medical devices using implanted leads.

A variety of different coverings have been used for implantable leads of medical devices to overcome the above limitations. Some coverings have involved metal or metal alloy wire being braided around the lead, thereby forming a shield having a large conductive surface area. Other coverings have involved the use of polymer-matrix composites. Such composite coverings, as opposed to metal wire coverings, are attractive due to their moldability. In addition, the composite coverings are more favorable because metal wire coverings can be prone to damage by scratching, abrasion, or wear.

Polymer-matrix composite coverings are conductive due to the presence therein of electrically conducting fillers, which can be discontinuous (e.g., such as particles or short fibers) or continuous (e.g., such as continuous fibers). As is known, even though they lack the continuity provided by continuous fillers, discontinuous fillers can just as well be used for electromagnetic shielding. Moreover, discontinuous fillers are suitable for composite fabrication by extrusion or injection molding and, if the discontinuous filler is fine enough in size, even by ink-jet printing or screen printing. Due to the lower cost and greater versatility of composite fabrication for discontinuous fillers compared to continuous fillers, discontinuous fillers have been widely used in making electrically conducting composites, especially those for electromagnetic shielding.

While polymer-matrix composites having discontinuous fillers have been used as lead coverings to reduce the effects of electromagnetic radiation, they have been found to present certain limitations, e.g., with respect to their overall shielding effectiveness. What is needed is apparatus used to reduce the potential adverse effects to medical devices, and in particular, to implantable electrical leads of the devices, when subjected to electromagnetic radiation, while further overcoming one or more of the limitations facing the discontinuous filler polymer-matrix composite lead coverings marketed to date.

BRIEF SUMMARY OF THE INVENTION

Embodiments of the invention relate to a medical electrical lead having a conductor assembly covered by an insulating layer, and a shield covering positioned adjacent or proximate to at least a portion of the insulating layer in order to shield the conductor assembly from one or more electromagnetic fields. The shield covering is formed of a polymer-matrix composite. The polymer-matrix composite includes a polymeric resin having discontinuous conductive fillers provided therein. The discontinuous conductive fillers include one or more of nano-sized metal structures and nano-sized non-metallic conductive structures. The nano-sized non-metallic conductive structures can have a coating formed of one or more metals. The nano-sized non-metallic conductive structures can be formed of carbon. In turn, the nano-sized non-metallic conductive structures can include one or more of carbon nanofibers, carbon filaments, carbon nanotubes, and carbon nanoflakes.

BRIEF DESCRIPTION OF THE DRAWINGS

FIG. 11 is a cross-sectional view of an implantable lead/extension having a further plurality of shield coverings, including those of FIGS. 8, 9, and 10, in accordance with certain embodiments of the invention.

FIG. 12 is a cross-sectional view of an implantable lead/extension having another further plurality of shield coverings, including those FIG. 8, in accordance with certain embodiments of the invention.

DETAILED DESCRIPTION OF THE PREFERRED EMBODIMENTS

Figure 1:
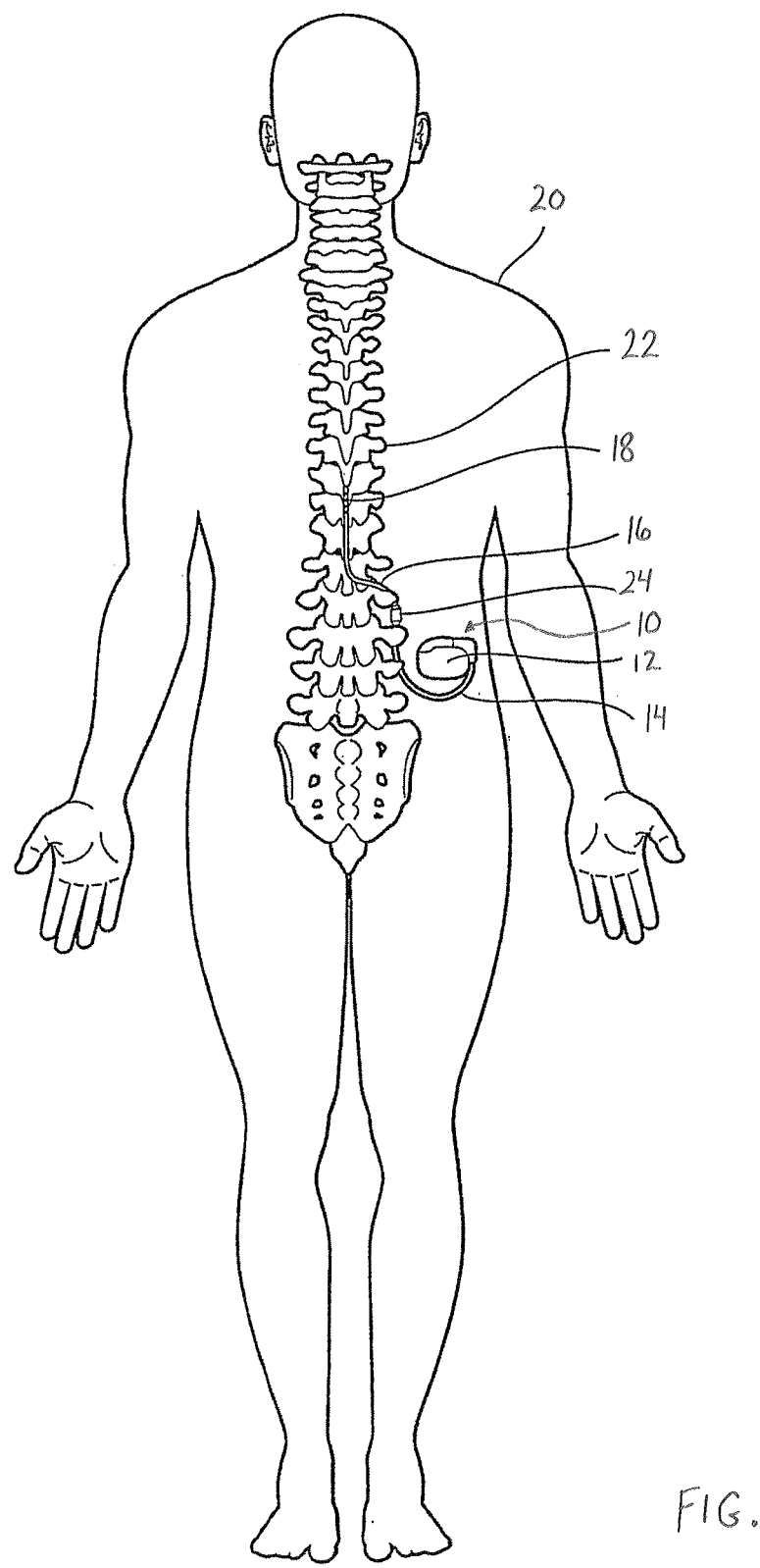
FIG. 1 is a perspective view of an exemplary IMD as provided in a patient in accordance with certain embodiments of the invention.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

Embodiments of the invention relate to medical devices, and specifically relate to shield coverings for leads extending between the devices and the patient. Embodiments described and illustrated herein pertain to implantable medical devices (IMDs); however, the invention can extend to any lead-bearing medical device, whether implantable or not. Furthermore, while the embodiments provided herein relate to certain IMDs, it should be appreciated that such embodiments are exemplary in nature. As such, the invention is not limited to any particular IMD, but instead is applicable to any IMD, including therapeutic and diagnostic devices, such as pacemakers, cardioverter/defibrillators, hemodynamic monitors, neurostimulators, and drug administering devices, as well as other devices for alleviating the adverse effects of various health ailments.

FIG. 1 illustrates an exemplary IMD in accordance with certain embodiments of the invention. The IMD 10 shown is a typical spinal cord stimulation (SCS) system and includes a pulse generator such as a SCS neurostimulator 12, a lead extension 14 having a proximal end coupled to the neurostimulator 12, and a lead 16 having a proximal end coupled to a distal end of the extension 14 and having a distal end coupled to one or more electrodes 18. The neurostimulator 12 is typically placed in the abdomen of a patient 20, and the lead 18 is placed somewhere along the patient's spinal cord 22. While only shown with a single lead 18, it is to be appreciated that the IMD 10, in certain embodiments, can have a plurality of leads. Such a system may also include a physician programmer and a patient programmer (not shown).

The neurostimulator 12 may be considered to be an implantable pulse generator and capable of generating multiple pulses occurring either simultaneously or one pulse shifting in time with respect to the other, and having independently varying amplitudes and pulse widths. The neurostimulator 12 contains a power source and electronics for sending precise, electrical pulses to the spinal cord 22 to provide the desired treatment therapy. While the neurostimulator 12 typically provides electrical stimulation by way of pulses, other forms of stimulation may be used such as continuous electrical stimulation.

The lead 16 includes one or more insulated electrical conductors each coupled at their proximal end to a connector 24 and to the electrodes 18 (or contacts) at its distal end. As is known, some leads are designed to be inserted into a patient percutaneously and some are designed to be surgically implanted. In certain embodiments, the lead 16 may contain a paddle at its distant end for housing the electrodes 18. In alternate embodiments, the electrodes 20 may comprise one or more ring contacts at the distal end of the lead 16.

While the lead 16 is shown as being implanted in position to stimulate a specific site in the spinal cord 22, it could also be positioned along the peripheral nerve or adjacent neural tissue ganglia or may be positioned to stimulate muscle tissue. Furthermore, electrodes 18 (or contacts) may be epidural, intrathecal or placed into spinal cord 22 itself. Effective spinal cord stimulation may be achieved by any of these lead placements. While the lead connector at proximal end of the lead 16 may be coupled directly to the neurostimulator 12, the lead connector is typically coupled to the lead extension 14 as is shown in FIG. 1.

Figure 2:
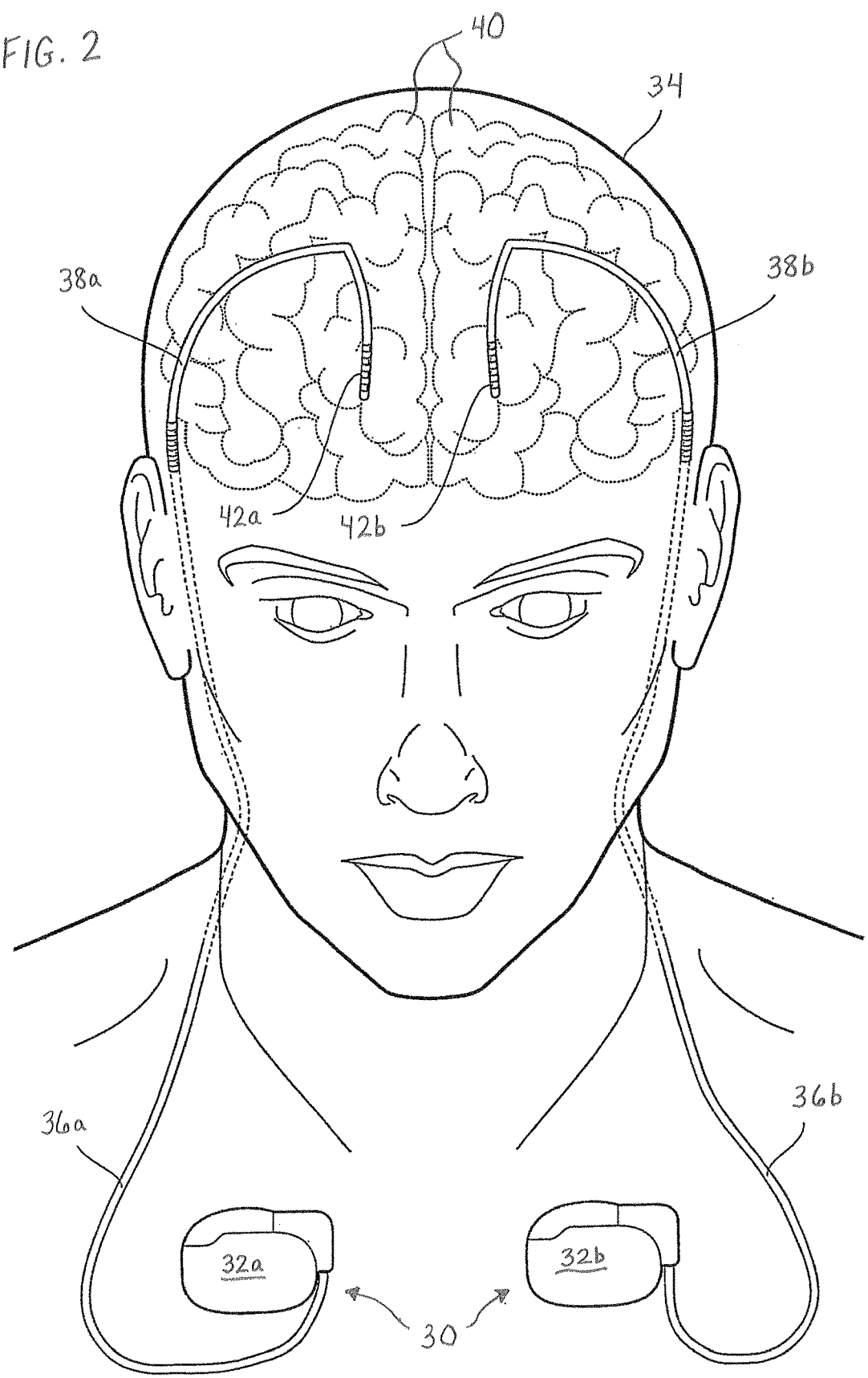
FIG. 2 is a perspective view of another exemplary IMD as provided in a patient in accordance with certain embodiments of the invention.

FIG. 2 illustrates another exemplary IMD in accordance with certain embodiments of the invention. The IMD 30 shown is a typical deep brain stimulation (DBS) system spinal cord stimulation (SCS) system and includes substantially the same components as does an SCS; that is, at least one neurostimulator, at least one extension, and at least one stimulation lead containing one or more electrodes. As can be seen, each neurostimulator 32a and 32b is implanted in the pectoral region of patient 34. Corresponding extensions 36a and 36b are deployed up through the patient's neck, and corresponding leads 38a and 38b are implanted in the patient's brain 40 as is shown at 42a and 42b. As can be seen, each of the leads 38 is connected to its respective extension 36 just above the ear on both sides of the patient 34.

Figure 3:
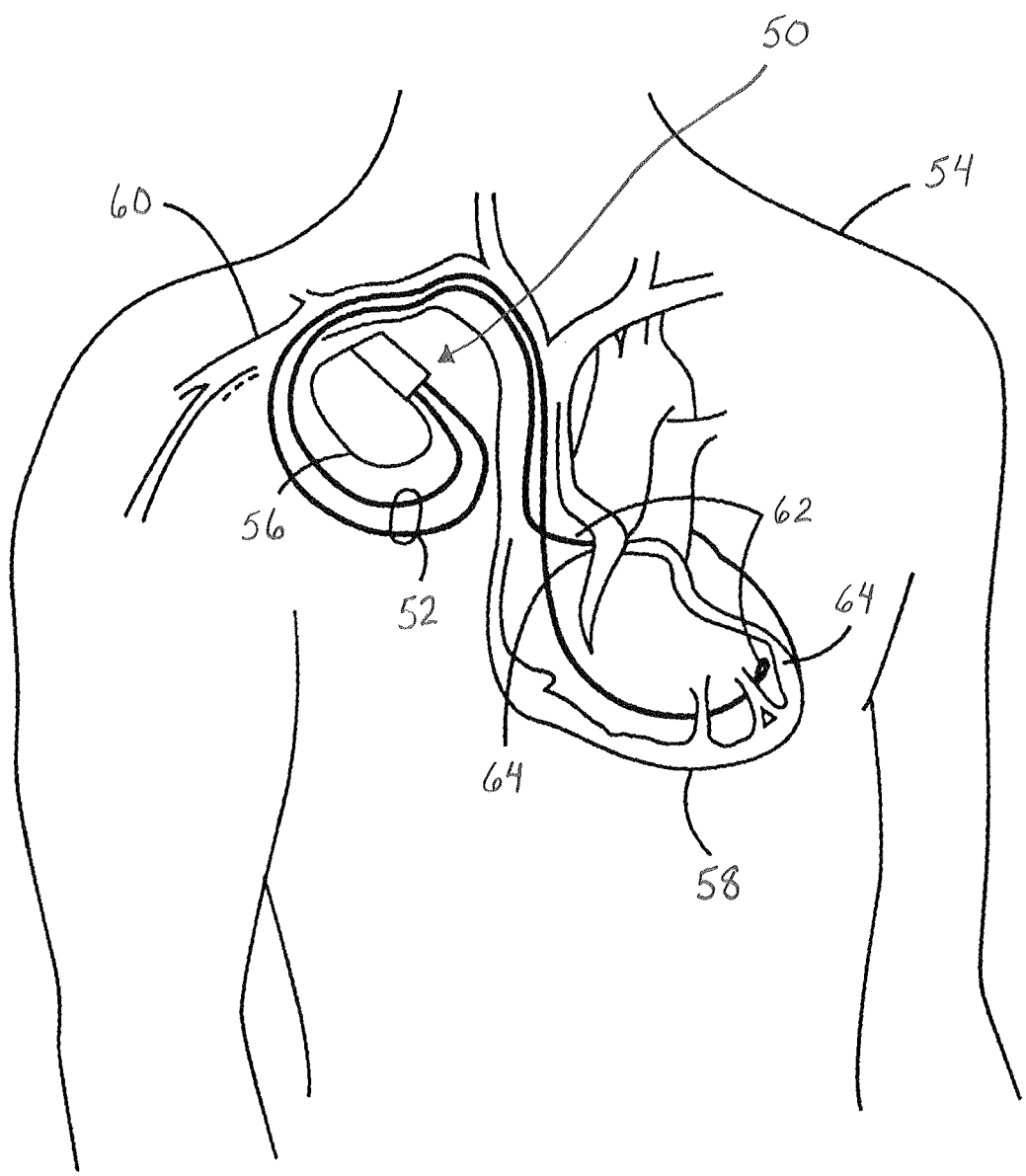
FIG. 3 is a perspective view of a further exemplary IMD as provided in a patient in accordance with certain embodiments of the invention.

FIG. 3 illustrates a further exemplary IMD in accordance with certain embodiments of the invention. The IMD 50 is a cardiac medical device, exemplarily shown as a pacemaker, and includes one or more leads 52 implanted in a patient 54. The leads 52 extend from the pacemaker can 56 and lead into the patient's heart 58 via a vein 60. Located generally near distal ends 62 of the leads 52 are one or more exposed conductive electrodes 64 that are attached to the heart tissue for sensing cardiac activity, delivering electrical pacing stimuli, and/or providing a cardioversion/defibrillation shock to the heart 58. The contact area between the electrodes 64 and the tissue of the heart 58 may be very small as compared, for example, to the contact area between the IMD 50 and the patient's body.

Implantable leads of IMDs similar to those described above in FIGS. 1-3, as well as implantable leads of other medical devices, have been equipped to reduce the effect from electromagnetic fields and/or radio-frequency energy, e.g., which can stem from MRI systems. To this end, the leads can be covered with polymer-matrix composites. Polymer-matrix composites, as used herein, include a polymeric resin having conductive fillers provided therein. As described above, the fillers can be discontinuous or continuous. As further described above, polymer-matrix composites having discontinuous fillers tend to be particularly attractive, as opposed to continuous filler composites, due to their lower cost and greater versatility of fabrication. Unfortunately, polymer-matrix lead coverings having discontinuous fillers have been found to present challenges, e.g., with respect to their overall shielding effectiveness.

One material that can be used when forming discontinuous fillers for use in polymer-matrix composites is carbon; however, the invention should not be limited to such. Instead, any other conductive material demonstrating similar advantageous properties, as described herein with respect to carbon, may be alternatively used. When provided in a discontinuous form, carbon can be presented in a wide variety of structures, including particulates, powders, fibers, filaments, flakes, and the like. In general, such structures are commercially available and practical to produce in sizes typically on the order of micrometers. For example, carbon filaments/fibers can be provided having outer diameters ranging in size from about 0.1 $\mu$m to about 12 $\mu$m. As should be appreciated, these diameter sizes are significantly reduced from the diameter sizes of commercially available metal wire (e.g., typically having minimum outer diameters of about 20 $\mu$m). As a result, such discontinuous carbon fillers are found to be less susceptible to the skin effect at high frequencies as compared to discontinuous metal wire fillers, as described below.

In general, when a static electrical field is applied to a conductor, the mobile charges therein, e.g., the electrons, are found to move and create a direct current (DC), which is uniformly distributed on the entire cross section of the conductor, resulting in a uniform current density. However, when an electromagnetic field is imposed on such a conductor, the mobile charges therein are found to oscillate back and forth with the same frequency as the impinging fields. The movement of these charges constitutes an alternating current (AC). Due to the attenuation of the electromagnetic waves in the conductor, the conductor's current density is greatest at the conductor's surface and declines exponentially as a function of depth. The decline in current density versus depth is known as the skin effect, and the skin depth is a measure of the distance over which the current falls from its value at the conductor's surface.

Figure 4:
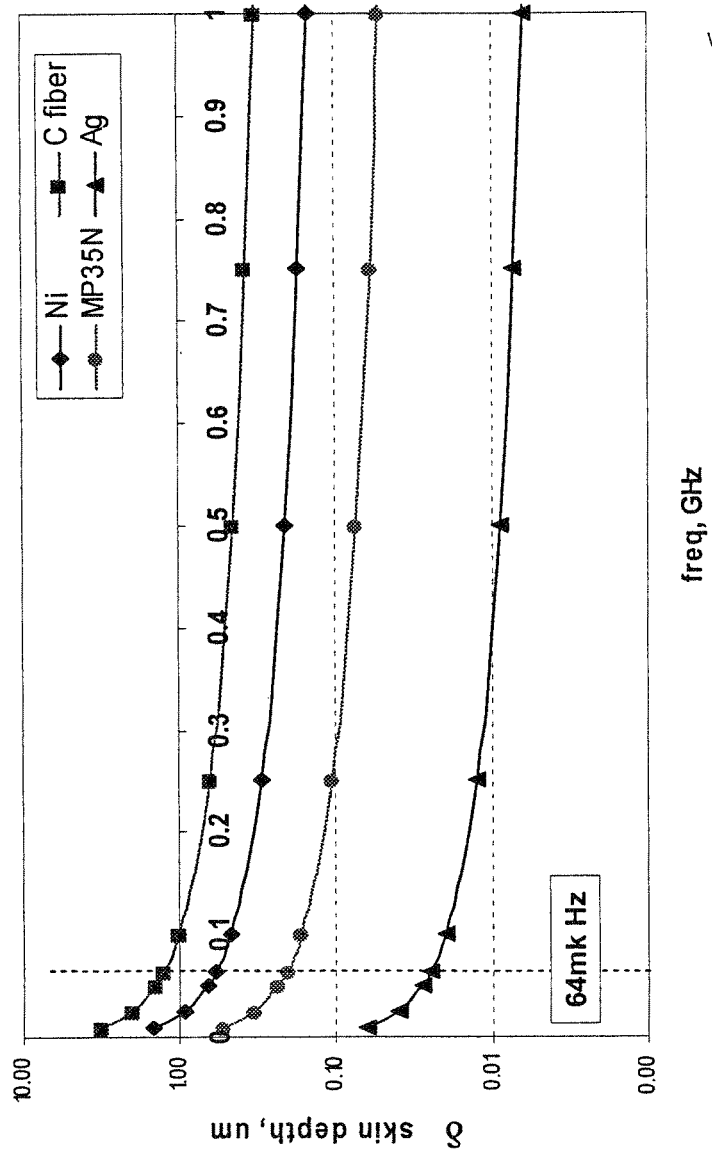
FIG. 4 is a plot generally showing skin depth for carbon and metals at high frequencies of electromagnetic fields.

FIG. 4 is a plot illustrating skin effect for carbon and a number of metals, illustrating the relationship described above. Specifically, the plot shows skin depth (in $\mu$m) for carbon and a number of metal wires at high frequencies (in GHz) of electromagnetic fields. As illustrated, skin depth for the materials generally decreases as frequency increases (with respect to electromagnetic fields surrounding the materials). Thus, while metals are generally known to exhibit high conductivity, the cross-sectional area of these metals which is actually usable for such purposes is limited due to the skin effect.

As shown, carbon is also limited due to the skin effect, but to a lesser extent than the metals. However, as described above, carbon fiber can be made having a smaller diameter than metal wire. As a result, a larger cross-sectional area of the carbon fiber can be used for conductive purposes in comparison to conventionally available metal wire. Therefore, carbon fiber can be found to be more efficient than metal wire, in particular, when used as a shield in the presence of high frequency electromagnetic fields. For example, as demonstrated in FIG. 4, skin depth of conductive metals is typically less than 1 $\mu$m when the frequency of surrounding electromagnetic fields is about 64 MHz or higher. As such, discontinuous metal fillers, even having minimum diameters of about 20 $\mu$m, are not very effective shields because much of their cross-sectional area would carry very little current. In contrast, discontinuous carbon fibers, which can be provided having outer diameters of about 0.1 $\mu$m to about 12 $\mu$m can be much more effective in their use as shields because a higher percentage of their cross section can be used for carrying current, and in turn, conducting.

As is known, for a polymer-matrix composite, the electromagnetic radiation shielding effectiveness increases with increasing filler volume fraction in the composite. However, the maximum filler volume fraction is limited by the poor composite mechanical properties at high filler volume fractions resulting from the poor filler-matrix bonding. As described above, discontinuous carbon can generally be preferable to discontinuous metal wire because a higher percentage of the cross-sectional area of the carbon can be used for conductivity purposes, particularly in the presence of high frequency electromagnetic fields. Though, even with this increased efficiency, the usable cross-sectional area of the carbon is generally found to be less conductive than metal wire. However, because the carbon, e.g., carbon fiber, is smaller in diameter than metal wire, a greater quantity of such carbon can be utilized in the matrix material. In turn, the increased efficiency of the carbon (as described above with respect to skin depth) with the greater quantity of carbon in the matrix material enables the carbon to collectively exhibit enhanced conductivity throughout the composite. As such, using micro-sized carbon in polymer-matrix composites provides a more effective shield as a lead covering in the presence of electromagnetic fields as opposed to metal wire.

Further, when fillers are provided that are conductive yet smaller in size than their alternatives, as is the case in the above example comparing micro-sized carbon and metal wire, the matrix material of the composite can also be reduced while still maintaining the warranted volume fractions of the composite. As a result, a thinner lead covering can be provided that is more effective at shielding the electrical lead. Further, provided the micro-sized carbon and other alternative filler material are comparable in price, materials and process savings can be realized by using micro-sized carbon while still providing good mechanical properties for the composite.

While the above embodiment demonstrates higher electromagnetic radiation shielding effectiveness being achieved when using micro-sized carbon instead of metal wire as discontinuous fillers in polymer-matrix composites, even higher shielding effectiveness can be achieved in such composites. As described above, carbon structures can be made discontinuous so as to have sizes on the order of micrometers. However, carbon structures can also be further reduced in size on the order of nanometers. Examples of such carbon structures include nanofibers, filaments, nanotubes, and nanoflakes. Alternatively, certain metals can be formed into nano-sized structures, e.g., particles and/or flakes, which would also be more effective as fillers in comparison to discontinuous wire or micro-sized carbon structures. Such fillers can include but are not limited to Ag, Au, Cu, Co, Ni, Pt, Sn, Ta, Ti, Zn, or any alloys thereof.

Accordingly, in certain embodiments, a polymer-matrix composite is provided having discontinuous fillers, with the fillers including one or more of nano-sized non-metallic conductive structures and nano-sized metal structures. The use of the term "structures" herein with respect to "nano-sized non-metallic conductive structures" and "nano-sized metal structures" is meant to indicate "one or more different structures" in making up the fillers in each case. In certain embodiments, as described above, the nano-sized non-metallic conductive structures can be formed of carbon. In turn, in certain embodiments, the nano-sized non-metallic conductive structures can include one or more of carbon nanofibers, carbon filaments, carbon nanotubes, and carbon nanoflakes. For example, carbon nanofibers are widely available from a number of commercial sources, one being Pyrograf Products, Inc., an affiliate of Applied Sciences, Inc., located in Cedarville, Ohio. One such carbon nanofiber provided by Pyrograf Products, Inc. is the Pyrograf®-III, ranging in diameter from about 70 and about 200 nanometers. In many cases, carbon nanofiber is commercially available ranging in diameter from about 70 to about 500 nanometers. The nano-sized metal structures can be introduced to the composite using commercially available nano-sized metal particles or by means of in-situ reduction of desired metal ions injected into the matrix via chemical method, metal ion implantation method, or other suitable methods.

As should be appreciated, similar to that already described above in comparing discontinuous fillers of conventional carbon structures and metal wire, when nano-sized carbon and/or nano-sized metal are used instead of the conventional micro-sized carbon and/or metals in forming the fillers, the resulting composites would have enhanced electromagnetic shielding effectiveness. As such, discontinuous fillers formed of nano-sized carbon structures and/or nano-sized metal structures, because of their reduced size (as compared to conventional micro-sized carbon and/or metals of same volume fraction), would be less susceptible to skin effect at high frequencies. Further, because of their reduced size, the discontinuous fillers formed of nano-sized carbon structures and/or nano-sized metal structures can be provided in increased quantity in the matrix material compared to micro-sized carbon fiber structures and discontinuous metal wire.

In some cases, nano-sized carbon structures may be selected over nano-sized metal structures. One reason may be due to cost considerations. However, as should be appreciated, using nano-sized carbon structures in polymer-matrix composites can be costly as compared to using conventional micro-sized carbon structures. One way to address this is to select the least costly of the carbon nano-sized structures. As is known, carbon nanofibers and carbon nanoflakes are less expensive to produce than carbon nanotubes. For example, material cost to produce one pound of Pyrograf®-III carbon nanofibers is less than $50, while producing the same amount of single walled carbon nanotubes, e.g., from CarboLex, Inc., located in Lexington, Ky., is about $16,030. As such, in terms of cost considerations, carbon nanofiber is generally preferred over carbon nanotubes.

Figure 5:
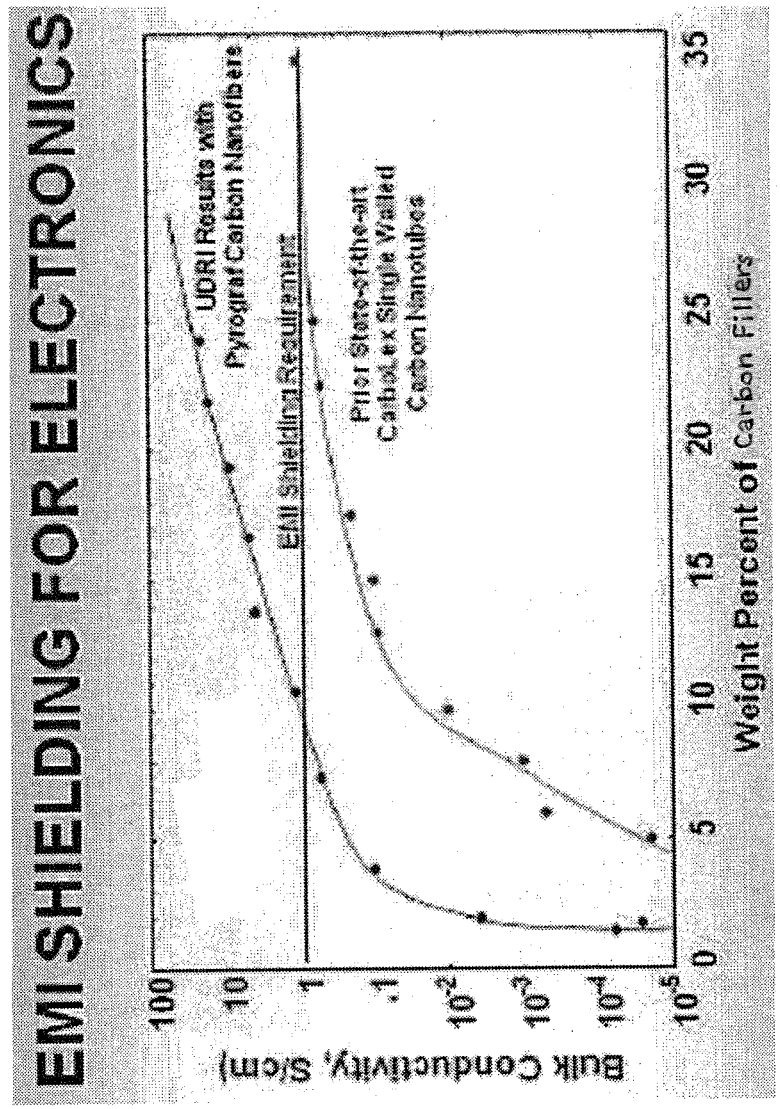
FIG. 5 is a plot generally showing conductivity of carbon nanofibers and carbon nanotubes at varying weight percentages of polymer-matrix composites.
Figure 6:
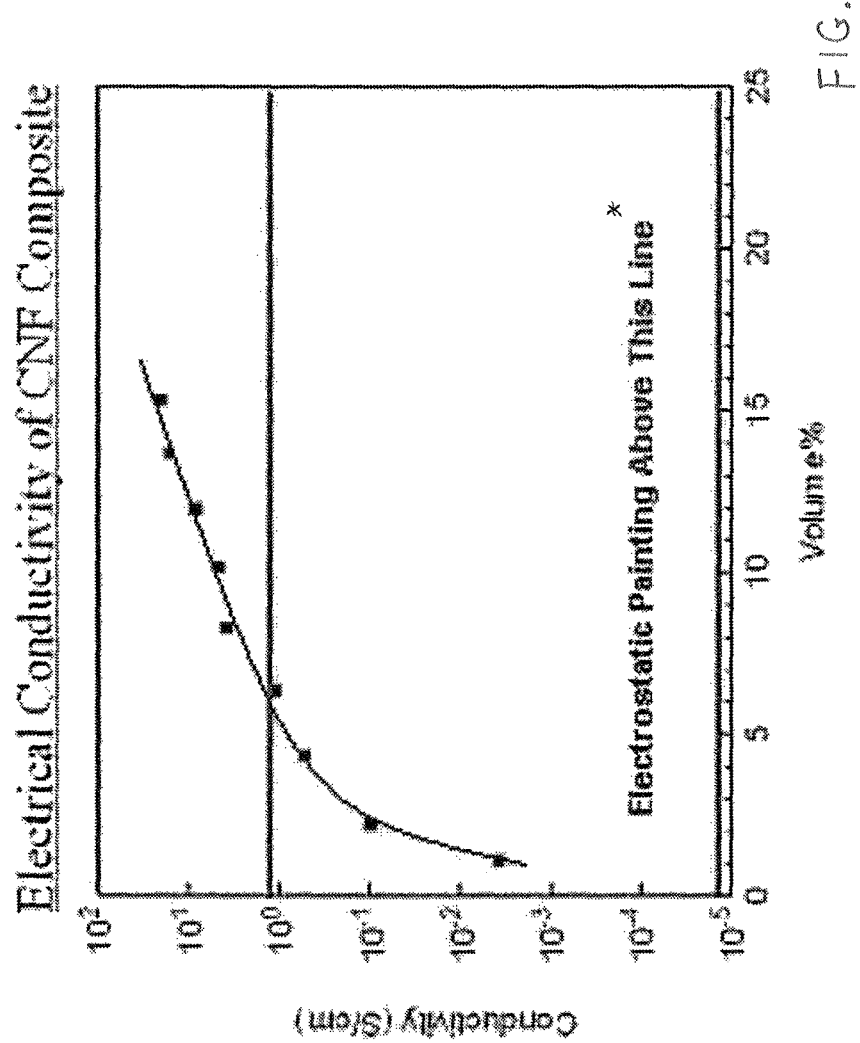
FIG. 6 is a plot generally showing conductivity of carbon nanofibers at varying volume percentages of polymer-matrix composites.

Further advantages in using carbon nanofiber are illustrated with respect to FIGS. 5 and 6. FIG. 5 is a plot illustrating electromagnetic shielding effect of carbon nanofibers and carbon nanotubes. Specifically, the plot shows bulk conductivity (in S/cm) for carbon nanofibers (from Pyrograf Products, Inc.) and single walled carbon nanotubes (from CarboLex, Inc.), given varying weight percentages of the carbon materials in polymer-matrix composites. As shown, the minimum requirement for electromagnetic shielding (about 1 S/cm) is initially met for carbon nanofibers when provided at about 10% weight of the composite, and then exceeded given greater weight percentages. In contrast, the minimum requirement for electromagnetic shielding is barely met by the carbon nanotubes, and only when the carbon nanotubes are provided at between about 25% and 30% weight of the composite. FIG. 6 is a plot illustrating conductivity (in S/cm) for carbon nanofibers, given varying volume percentages in polymer-matrix composites. As shown, the curve is similar to the one shown in FIG. 5 for carbon nanofibers, where the minimum requirement for electromagnetic shielding (about 1 S/cm) is initially met for the carbon nanofibers when provided at about 7% weight of the composite, and then exceeded given greater weight percentages. In summary, carbon nanofibers demonstrate significantly higher electromagnetic shielding effectiveness as compared to carbon nanotubes.

One challenge encountered to date in using nano-sized carbon structures as discontinuous fillers in polymer-matrix composites is their natural tendency to clump together. As such, effective dispersion of the nano-sized carbon structures throughout the matrix material can be difficult, which in turn, can compromise the shielding effectiveness of such composites. For example, if a quantity of carbon nanofibers is selected based on a uniform distribution throughout the matrix material, if the fibers clump, this uniform distribution would be difficult to achieve. In turn, the shielding effectiveness would likely not be uniformly dispersed through the composite, leaving some areas more susceptible to penetration by electromagnetic radiation.

It has been found through experimentation that this clumping phenomenon of nano-sized carbon structures can be overcome. Specifically, by providing a thin coating of metal on the nano-sized carbon structures prior to their disbursement in matrix material when forming polymer-matrix composites, one can offset the natural tendency of the nano-sized carbon structures to clump together. As a result, uniform shielding effectiveness for the composite can be achieved using nano-sized carbon structures, e.g., carbon nanofibers, which have a tendency to clump together. As such, in certain embodiments, carbon nanofibers, carbon filaments, carbon nanotubes, and carbon nanoflakes used as fillers can be provided with a metal coating. Such metal coating, in certain embodiments, can be provided so as to be no greater than about 1 μm. Metalization of carbon nanofibers, carbon filaments, carbon nanotubes, and carbon nanoflakes can be achieved via physical vapor deposition, chemical vapor deposition, auto-catalytic electroless deposition, or other metallization techniques known to the art. The metal coating can include but are not limited to Ag, Au, Cu, Co, Ni, Pt, Sn, Ta, Ti, Zn, alloys thereof, as well as any combination thereof.

Figure 7:
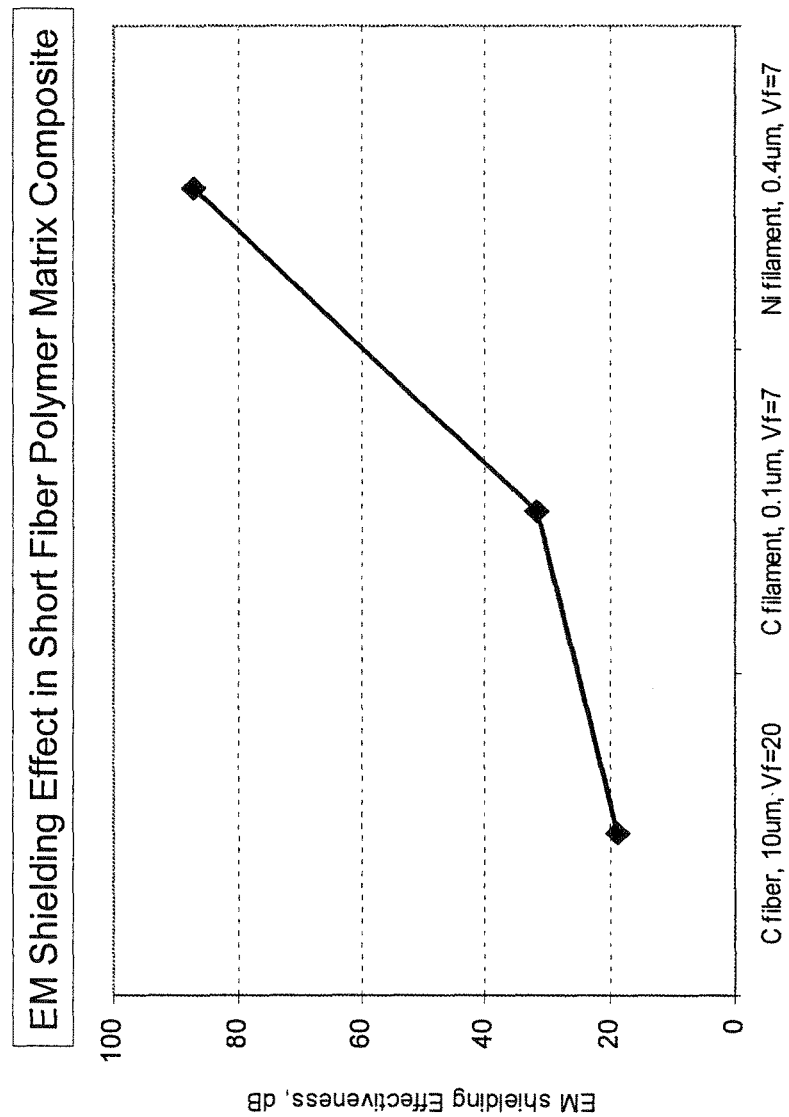
FIG. 7 is a plot generally showing electromagnetic shielding effectiveness of carbon micro fiber, carbon filament, and nickel filament.

It should be appreciated that such metal coating also enhances the conductivity, and thus, shielding effectiveness, of the carbon structures. For example, the metal coating can be made of nickel. FIG. 7 shows electromagnetic shielding effectiveness of carbon fiber, carbon filament, and nickel filament, each at commercially available diameter sizes. Of the three, the nickel filament demonstrates the highest electromagnetic shielding effectiveness, where the volume fraction of the nickel filament indicates that such composite can be processed, e.g., as tubing, to be used as a coating for discontinuous fillers in polymer-matrix composites.

Figure 8:
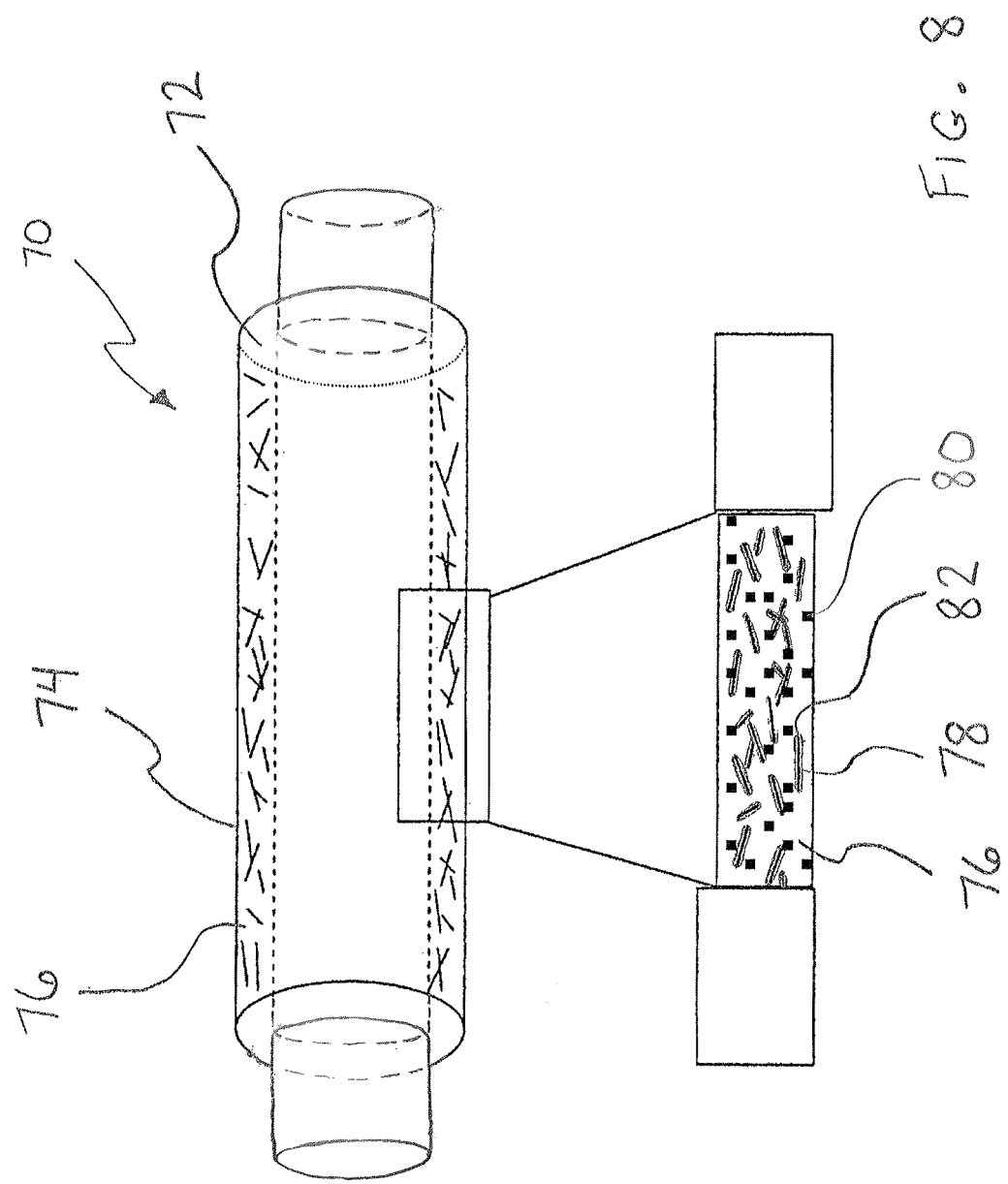
FIG. 8 is a perspective view of a partial implantable lead/extension having a shield covering in accordance with certain embodiments of the invention.

FIG. 8 illustrates a perspective view of a partial implantable lead/extension having a shield covering in accordance with certain embodiments of the invention. As shown, the lead/extension 70 includes a conductor assembly having one of more conductors (not shown) covered by an insulating layer 72. As should be appreciated, the one or more conductors can be formed of any suitable metal having conductive properties, such as Cu, Al, Ag, alloys thereof or other alloys (e.g., superalloy MP35N), mixtures thereof, and the like. Further, as should be appreciated, each of the one or more conductors can be configured into one of a wide variety of shapes, e.g., generally straight, helically wound, etc. The insulating layer 72 is generally formed of silicone, a biocompatible polymer such as polyurethane, or any suitable biocompatible, non-conducting material known in the art.

As shown, the lead/extension 70 has a shield covering 74, which functions to shield electromagnetic radiation from the lead conductors. In certain embodiments, the shield covering 74 is provided as a polymer-matrix composite. As described herein, the polymer-matrix composite generally includes a polymeric resin 76 having conductive fillers provided therein. As shown, in certain embodiments, the conductive fillers are discontinuous conductive fillers. The discontinuous conductive fillers, in certain embodiments, can be nano-sized non-metallic conductive structures 78, nano-sized metal structures 80, or the combination of both (as exemplarily shown in FIG. 8). The distribution of the fillers can be uniformly distributed throughout the composite matrix (as illustrated in FIG. 8), or gradiently distributed with higher concentration at the surface of the shield tube (not shown in the Figure) so as to take advantage of both shield effect and mechanical properties of the polymer composite tube. The polymeric resin may be selected from any of a wide variety of thermoplastic resins and elastomers, blends of thermoplastic resins, and/or thermoset resins. Some non-limiting examples of each of these resin types are provided in U.S. patent application Ser. No. 09/683,069, entitled "Conductive Plastic Compositions and Method of Manufacture Thereof", incorporated herein in relevant part.

As described above, in certain embodiments, the nano-sized non-metallic conductive structures 78 can be formed of carbon. The carbon structures, in certain embodiments, can include one or more of carbon nanofibers, carbon filaments, carbon nanotubes, and carbon nanoflakes. As should be appreciated, when the nano-sized carbon structures are selected, one would need to select the particular grade for the structures. For example, as is known, there are many grades of carbon fibers commercially available. As such, one would select the grade which has or is able to be produced to have a desirable diameter dimension, yet also exhibits low electrical resistivity and high strength properties. In certain embodiments, the fillers have an outer diameter ranging in size from about 70 nanometers to about 500 nanometers.

As further shown, in certain embodiments, the nano-sized non-metallic conductive structures 78 are each coated with a metal coating 82, including but not limited to Ag, Au, Cu, Co, Ni, Pt, Sn, Ta, Ti, Zn, alloys thereof, as well as any combination thereof. As such, the nano-sized non-metallic conductive structures 78 can be prevented from clumping so as to be uniformly disbursed in the resin 76 and the conductivity of the fillers can be enhanced. The covering 74 is not in direct electrical contact with the conductors of the conductor assembly of the lead/extension 70. In certain embodiments, the covering 74 can be in contact with the housing of the medical device (e.g., IMD) from which they stem, where the device can act as an additional surface for dissipation of energy received by the covering 74 from electromagnetic radiation.

It should be appreciated that the lead/extension 70 can be either a lead, an extension for a lead, or both. For example, with respect to the IMD 10 of FIG. 1, the leads 16, the lead extensions 14, or both, can be equipped with the covering 74. The above similarly holds true for the leads 38a, 38b and extensions 36a, 36b with respect to the IMD 30 of FIG. 2.

The amount of the discontinuous fillers, or combinations of fillers formed of different materials, to be incorporated into the matrix material can vary depending on the desired properties exhibited by the particular medical device or medical device component. As described above, enough of the discontinuous fillers should be included so that desired properties are at least minimally exhibited by the composite, but not so much of the fillers should be included so as to have a detrimental effect on the properties of the composite. While the particular range may vary depending on the filler and matrix materials being utilized, composites exhibiting advantageous properties can be obtained by incorporating from about 0.005% to about 99% filler material relative of the total final composition weight of the composite. In many embodiments, filler material may be incorporated in an amount of from about 0.01% up to about 40% or 50% by weight of the composite. In a typical embodiment, the filler material can be incorporated in an amount of from about 0.1% to about 20% of the composite, for example, from about 1% to about 10% by weight of the composite.

Each of FIGS. 9-12 shows a cross-sectional view of an implantable lead having a plurality of shielding coverings in accordance with certain embodiments of the invention. Each of the implantable leads/extensions of FIGS. 9-12 includes the insulating layer 72 and the covering 74 shown and described in FIG. 8. Further, each of the leads/extensions 70 of FIGS. 9-12 includes one or more additional layers located proximate or adjacent to the covering 74. While each of the insulating layers 72, the coverings 74, and the one or more additional layers are shown to have similar thicknesses in FIGS. 9-12, such is done to merely show the proper position of the layers with respect to one another. As such, the invention should not be limited by the thickness of the layers represented in FIGS. 9-12.

Figure 9:
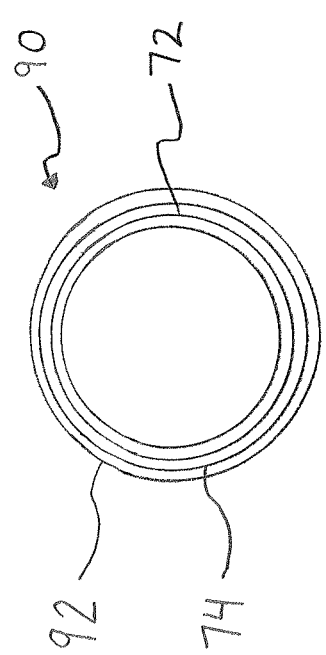
FIG. 9 is a cross-sectional view of an implantable lead/extension having a plurality of shield coverings, including those of FIG. 8, in accordance with certain embodiments of the invention.

FIG. 9 illustrates lead/extension 90. In certain embodiments, as shown, a coating 92 lies external to the covering 74. In certain embodiments, the coating 92 comprises one or more metals. As such, the coating 92 is adapted to enhance the shielding effect of the lead/extension 90. In certain embodiments, the one or more metals can include Ag, Au, Cu, Co, Ni, Pt, Sn, Ta, Ti, Zn, alloys thereof, as well as any combination thereof; however, the invention should not be limited to such. Instead, the one or more metals can include any metal or combination of metals which can be used in conjunction with the covering 74 to enhance the shielding effect of the lead/extension 90. In certain embodiments, if the coating 92 is to be kept thin, the coating 92 may be applied to the covering 74 via sputtering, physical vapor deposition, chemical vapor deposition, auto-catalytic electroless deposition, electrolytic deposition, or by any other suitable application method.

Figure 10:
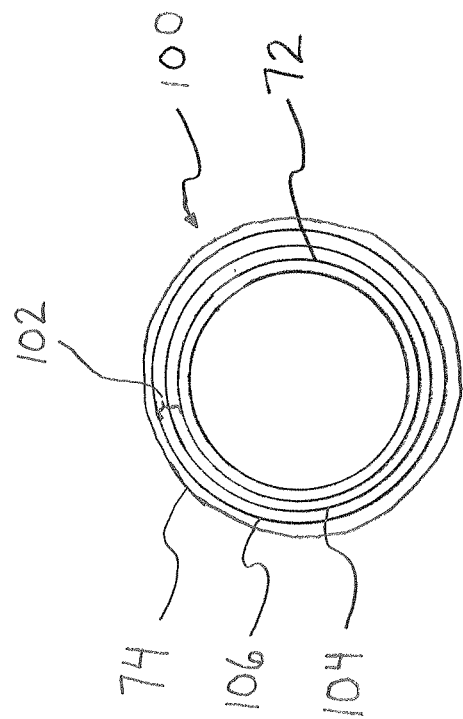
FIG. 10 is a cross-sectional view of an implantable lead/extension having another plurality of shield coverings, including those of FIG. 8, in accordance with certain embodiments of the invention.

FIG. 10 shows lead/extension 100. In certain embodiments, as shown, additional layers 102 lie internal to the covering 74; however, the invention should not so limited, as the additional layers 102, while not shown as such, can alternatively lie external to the covering 74 just as well. In certain embodiments, the layers 102 are formed of a braided metal sheath or mesh 104 with an optional outer insulation layer 106. As such, the additional layers 102 are adapted to enhance the shielding effect of the lead/extension 100. In addition, the layers 102 are useful for increasing the torsional stiffness of the conductor assembly, thereby aiding the insertion of the lead/extension 100 within the patient. In certain embodiments, the braided metal sheath or mesh 104 can be formed of Ni, Ta, Ti, or superalloy MP35N; however, the invention should not be limited to such. Instead, the metal sheath or mesh 104 can include any metal or combination of metals or alloys which can be used to enhance the shielding effect of the lead/extension 100. When used, the outer insulation layer 106 can be formed of silicone, a biocompatible polymer such as polyurethane, or any suitable biocompatible, non-conducting material known in the art.

FIG. 11 illustrates lead/extension 110. As can be appreciated, the lead/extension 110 is a combination of lead/extension 90 of FIG. 9 and lead/extension 100 of FIG. 10. As such, the lead/extension 110 has the coating 92 (as described above with respect to FIG. 9) lying external to the covering 74 and the additional layers 102 (as described above with respect to FIG. 10) lying either internal (as shown) or external to the covering 74. As described above, the coating 92 and the additional layers 102 are used in combination to enhance the shielding effect of the lead/extension 110.

FIG. 12 shows lead/extension 120. In certain embodiments, as shown, a further layer 122 lies internal to the covering 74. The layer 122 is formed of a conductive non-metallic material that is in a wrapped or woven form. Such conductive non-metallic materials and embodiments in which the materials are used for medical device lead shielding are described in more detail in the U.S. patent application entitled "Continuous Conductive Materials for Electromagnetic Shielding", which is filed concurrently herewith and incorporated herein in its entirety. In certain embodiments, the conductive non-metallic material can be carbon. The carbon, in certain embodiments, is formed of one or more of carbon fiber, carbon nanofiber, and carbon nanotube having one or more of single and multiple walls. In certain embodiments, the conductive material has an outer diameter that is preferably no greater than about 20 μm (generally representing minimum diameter of metal wire), and more preferably, no greater than about 12 μm. The conductive material, in certain embodiments, has a higher skin depth than metals. In certain embodiments, the conductive non-metallic material is covered with a metal coating, thereby enhancing the conductivity of the layer 122. In summary, the layer 122 is adapted to enhance the shielding effect of the lead/extension 120. While the layer 122 is shown to be internal to the covering 74, the invention should not be limited to such, as the layer 122 could just as well be switched in position with the covering 74 (so that the further layer 122 lies external to the covering 74) so as to still enhance the shielding effect of the lead/extension 120.

In certain embodiments, the lead/extension 120 of FIG. 12 may further contain one or more of the coating 92 of FIG. 9 and the additional layers 102 of FIG. 10 to further enhance the shielding effect of the lead/extension 120. If the coating 92 is included on the lead/extension 120, in certain embodiments, the coating 92 can lie external to one or more of the continuous conductive fiber layer 122 and the covering 74. If the additional layers 102 are included on the lead/extension 120, in certain embodiments, the additional layers 102 can lie internal or external to the continuous conductive fiber layer 122, and internal or external to the covering 74.

It will be appreciated the embodiments of the present invention can take many forms. The true essence and spirit of these embodiments of the invention are defined in the appended claims, and it is not intended the embodiment of the invention presented herein should limit the scope thereof.

What is claimed is:

1. A medical electrical lead, comprising:
a conductor assembly having one or more conductors covered by an insulating layer; and
a shield covering adjacent or proximate to at least a portion of the insulating layer to shield the conductors from one or more electromagnetic fields, the shield covering comprising a polymer-matrix composite, the polymer-matrix composite including a polymeric resin having discontinuous conductive fillers provided therein, the discontinuous conductive fillers comprising nano-sized non-metallic conductive structures, the discontinuous conductive fillers being gradiently distributed radially at least within a continuous portion of the polymer-matrix composite with a greater concentration at the surface of the shield covering and being uniformly distributed circumferentially and longitudinally at the surface of the polymer-matrix, the shield covering being circumferentially and longitudinally continuous over an entire length of the shield covering.

2. The medical electrical lead of claim 1, wherein the nano-sized non-metallic conductive structures are formed of carbon.

3. The medical electrical lead of claim 2, wherein the nano-sized non-metallic conductive structures comprise one or more of carbon nanofibers, carbon filaments, carbon nanotubes, and carbon nanoflakes.

4. The medical electrical lead of claim 3, wherein the nano-sized non-metallic conductive structures comprise carbon nanofibers.

5. The medical electrical lead of claim 4, wherein the carbon nanofibers have an outer diameter ranging in size from about 70 nanometers to about 500 nanometers.

6. The medical electrical lead of claim 1, further comprising a further layer formed of a conductive non-metallic material being in a wrapped or woven form, the further layer positioned either internal or external to the shield covering, the further layer and the shield covering providing an enhanced shielding effect for the one or more conductors.

7. The medical electrical lead of claim 6, wherein the conductive non-metallic material has a higher skin depth than metals.

8. The medical electrical lead of claim 6, wherein the conductive non-metallic material has an outer diameter that is no greater than about 20 μm.

9. The medical electrical lead of claim 6, wherein the conductive non-metallic material comprises carbon.

10. The medical electrical lead of claim 1, wherein the nano-sized non-metallic conductive structures each has an outer metal coating.

11. The medical electrical lead of claim 10, wherein the outer metal coating prevents a natural tendency of the structures from clumping together.

12. The medical electrical lead of claim 10, wherein the outer metal coating enhances electromagnetic radiation shielding effectiveness of the nano-sized non-metallic conductive structures, the outer metal coating having a thickness of no greater than about 1 μm.

13. The medical electrical lead of claim 1, further comprising a coating formed of one or more metals, the coating positioned external to the shield covering, the coating and the shield covering providing an enhanced shielding effect for the one or more conductors.

14. The medical electrical lead of claim 1, further comprising one or more additional layers positioned internal to the shield covering, one of the additional layers comprising a braided metal sheath or mesh, the one additional layer and the shield covering providing an enhanced shielding effect for the one or more conductors.

15. The lead of claim 1, wherein the lead is coupled to a medical device.

16. An implantable medical lead for alleviating the adverse effects of various health ailments of a patient comprising:
a lead body having a proximal end and a distal end, the distal end;
one or more electrodes or electrical contacts for sensing and/or therapy delivery on the lead body;
a conductor assembly having one or more conductors covered by an insulating layer of the lead body;
a shield covering coupled to the lead body and comprising a polymer-matrix composite, the polymer-matrix composite including a polymeric resin having discontinuous conductive fillers provided therein, the discontinuous conductive fillers comprising nano-sized non-metallic conductive structures, the discontinuous conductive fillers being gradiently distributed radially at least within a continuous portion of the polymer-matrix composite with a greater concentration at the surface of the shield covering and being uniformly distributed circumferentially and longitudinally at the surface of the polymer-matrix, the shield covering being circumferentially and longitudinally continuous over an entire length of the shield covering.

17. The lead of claim 16, wherein the lead is coupled to a medical device.

18. An implantable medical lead for alleviating the adverse effects of various health ailments of a patient comprising:
a lead body having a proximal end and a distal end, the distal end;
one or more electrodes or electrical contacts for sensing and/or therapy delivery on the lead body;
a conductor assembly having one or more conductors covered by an insulating layer of the lead body;
a shield covering adjacent in a radial direction or proximate in the radial direction to at least a portion of the insulating layer to shield the conductors from one or more electromagnetic fields, the shield covering comprising a polymer-matrix composite, the polymer-matrix composite including a polymeric resin having discontinuous conductive fillers provided therein, the discontinuous conductive fillers comprising nano-sized non-metallic conductive structures, the discontinuous conductive fillers being gradiently distributed radially at least within a continuous portion of the polymer-matrix composite with a greater concentration at the surface of the shield covering and being uniformly distributed circumferentially and longitudinally at the surface of the polymer-matrix, the shield covering being circumferentially and longitudinally continuous over an entire length of the shield covering.

19. The lead of claim 18, wherein the lead is coupled to a medical device.

* * * * *